US006410473B1

(12) United States Patent
Pinnavaia et al.

(10) Patent No.: US 6,410,473 B1
(45) Date of Patent: *Jun. 25, 2002

(54) QUASI CRYSTALLINE INORGANIC OXIDE COMPOSITIONS PREPARED BY NEUTRAL TEMPLATING ROUTE

(75) Inventors: Thomas J. Pinnavaia; Wenzhong Zhang, both of East Lansing; Thomas R. Pauly, Lansing, all of MI (US); Peter T. Tanev, Katy, TX (US)

(73) Assignee: Board of Trustees of Michigan State University, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/541,728

(22) Filed: Apr. 3, 2000

Related U.S. Application Data

(60) Division of application No. 09/192,172, filed on Nov. 13, 1998, which is a continuation-in-part of application No. 08/355,979, filed on Dec. 14, 1994, now Pat. No. 5,840,264, which is a continuation-in-part of application No. 08/293,806, filed on Aug. 22, 1994, now abandoned, and a continuation-in-part of application No. 08/527,504, filed on Sep. 13, 1995, now Pat. No. 5,672,556.

(51) Int. Cl.$^7$ .............................................. C01B 33/38
(52) U.S. Cl. ........................ 502/74; 423/277; 423/326; 423/705
(58) Field of Search ............................. 502/74, 80, 84; 423/277, 326, 705

(56) References Cited

U.S. PATENT DOCUMENTS

| | | | |
|---|---|---|---|
| 3,702,886 A | 11/1972 | Argauer et al. | |
| 3,709,979 A | 1/1973 | Chu | |
| 4,108,881 A | 8/1978 | Rollmann et al. | |
| 4,151,189 A | 4/1979 | Rubin et al. | |
| 4,391,785 A | 7/1983 | Rosinski et al. | |
| 4,619,820 A | 10/1986 | Valyocsik | |
| 4,910,006 A | 3/1990 | Zones et al. | |
| 5,098,684 A | 3/1992 | Kresge et al. | |
| 5,102,643 A | 4/1992 | Kresge et al. | |
| 5,143,879 A | 9/1992 | Whitehurst | |
| 5,622,684 A | * 4/1997 | Pinnavaia et al. | 423/702 |
| 5,672,556 A | * 9/1997 | Pinnavaia et al. | 502/63 |
| 5,800,800 A | * 9/1998 | Pinnavaia et al. | 423/702 |
| 5,840,264 A | * 11/1998 | Pinnavaia et al. | 423/277 |
| 6,193,943 B1 | * 2/2001 | Pinnavaia et al. | 423/326 |

OTHER PUBLICATIONS

Breck D. W., Zeolite Molecular Sieves: Structure, Chemistry and Use; Wiley and Sons London, 1974.
Meier, et al., Atlas of Zeolite Structure Types, Butterworth, London, 1992.
Barrer, et al., Zeolites, vol. 1, 30–140 (1981).
Lok, et al., Zeolites, vol. 3, 282–291 (1983).
Davis, et al., Chem. Mater., vol. 4, 756–768 (1992).
Gies, et al., Zeolites, vol. 12, 42–49 (1992).
Hearmon, et al., Zeolites, vol. 10, 608–611 (1990).
Davis, et al., Nature, vol. 331, 698–699 (1988).
Estermann, M., et al., Nature, vol. 352, 320–323 (1991).
Hso et al., J. Chem. Soc. Chem. Commun., 875–876 (1992).
Soghmonian, et al., Angew. chem., Int. Ed. Engl. vol. 32, 610–611 (1993).
Beck, et al., J. Am. Chem. Soc., vol. 114, 10834–10843 (1992).
Inagaki, et al., J. Chem. Soc. Chem. Commun., vol. 8, 680–682 (1993).
Huo, et al., Nature, vol. 368, 317–321 (1994).
Pinnavaia, et al., Nature, vol. 386, 321–323 (1994).
Sing, et al., Pure Appl. chem., vol. 57, 603–619 (1985).
Perspectives in Molecular Sieve Science, Eds. Flank, W. H. and White T. E. Jr., ACS symposium series. No. 368, Washington, D.C., pp 247; 524; 544 (1988).
Gunnawardane, et al., Zeolites, vol. 8, 127–131 (1988).
Davis, et al., XIII North American Meeting of the Catalysis Soc., Book of Abstracts, p. D14 (1993).
Branton et al., J. Chem. Soc., Chem. Commun., 1257–1258 (1993).
Chavin, et al., J. Catal., vol. 111, 94–105 (1988).
Cartlidge, et al., Zeolites, vol. 9, 346–349 (1989).
Sachtler, W.M.H., Catal. Today 15, 419–429 (1992).
Schmidt, R.E., et al., J. Am. Chem. Soc., 117; 4049 (1995).
Mukerjee, P., et al., J. Phys. Chem. 82:1620 (1978).
Gordon, J. E., et al., J. Phys. chem. 74:957 (1970).
Horvath, G., et al., J. Chem. Eng. Jpn. 16:470 (1983).
Tanev, P.T., et al., Science 267:865 (1995).
Tanev, P.T., et al., Nature 368:321 (1994).
Chen, C.Y., et al., Microporous Mater. 4:1 (1995).
Bagshaw, S. A., et al., Science 269:1242 (1995).
Bagshaw, S.A., et al., Angnew, Chem. Int. Ed. Engl. 35:1102 (1996).
Prouzet, E., et al., Angnew, chem Int. Ed. Engl. 36:517 (1997).
Ryoo, R., et al., J. Phy. Chem 100:17718 (1996).

* cited by examiner

Primary Examiner—Stuart L. Hendrickson
(74) Attorney, Agent, or Firm—Ian C. McLeod

(57) ABSTRACT

Crystalline inorganic oxide compositions having regular wormhole-like channels are described. The formation of the mesoporous composition is accomplished by hydrogen bonding between a neutral amine template in water and a water miscible organic solvent and a neutral inorganic oxide precursor, wherein there is an excess of an alkanol or water used to dissolve the template. The template can be removed and recycled.

16 Claims, 10 Drawing Sheets

QUASI CRYSTALLINE INORGANIC OXIDE COMPOSITIONS PREPARED BY NEUTRAL TEMPLATING ROUTE

CROSS-REFERENCE TO RELATED APPLICATION

This application is a division of Ser. No. 09/192,172, filed Nov. 13, 1998, continuation-in-part of which is pending U.S. application Ser. No. 08/355,979, filed Dec. 14, 1994, U.S. Pat. No. 5,840,264 which in turn is a continuation-in-part of application 08/293,806 filed Aug. 22, 1994, now abandoned, and 08/527,504, filed Sep. 13, 1995 which is now U.S. Pat. No. 5,672,556.

U.S. GOVERNMENT RIGHTS

The invention described in this application was sponsored by the National Science Foundation Contract CHE-9633798. The U.S. Government has certain rights to this invention.

BACKGROUND OF THE INVENTION

(1) Field of the Invention

This invention relates to new mesoporous quasi crystalline inorganic oxide compositions having regular worm hole shaped channels. In particular, the present invention relates to those compositions formed by a novel self-assembly method comprising steps of hydrogen bonding between a neutral amine template in water and a water miscible organic solvent with a substantial excess of the water or the solvent, and a neutral inorganic oxide precursor, followed by hydrolysis and crosslinking. This invention also relates to a route for facile recovery and recycling of the template by simple solvent extraction.

(2) Description of Related Art

Porous solids created by nature or by synthetic design have found great utility in all aspects of human activity. The pore structure of the solids is usually formed in the stages of crystallization or subsequent treatment. Depending on their predominant pore size, the solid materials are classified as: (i) microporous, having pore sizes <20 Å; (ii) macroporous, with pore sizes exceeding 500 Å; and (iii) mesoporous, with intermediate pore sizes between 20 and 500 Å. The use of macroporous solids as adsorbents and catalysts is relatively limited due to their low surface area and large non-uniform pores. Microporous and mesoporous solids, however, are widely used in adsorption, separation technology and catalysis. Owing to the need for higher accessible surface area and pore volume for efficient chemical processes, there is a growing demand for new highly stable mesoporous materials. Porous materials can be structurally amorphous, paracrystalline, or crystalline. Amorphous materials, such as silica gel or alumina gel, do not possess long range order, whereas paracrystalline solids, such as γ- or η- $Al_2O_3$ are quasiordered as evidenced by the broad peaks on their X-ray diffraction patterns. Both classes of materials exhibit a broad pore size distribution of pores predominantly in the mesoporous range. This wide pore size distribution limits the shape selectivity and the effectiveness of the adsorbents, ion-exchanges and catalysts prepared from amorphous and paracrystalline solids.

The only class of porous materials possessing rigorously uniform pore sizes is that of zeolites and related molecular sieves. Zeolites are microporous highly crystalline aluminosilicates. Their lattice is composed by $IO_4$ tetrahedra (I=Al and Si) linked by sharing the apical oxygen atoms. Their pore network, which is confined by the spatially oriented $IO_4$ tetrahedra, consists of cavities and connecting windows of uniform size (Breck D. W., *Zeolite Molecular Sieves: Structure, Chemistry and Use*; Wiley and Sons; London, 1974). Because of their aluminosilicate composition and ability to discriminate small molecules, zeolites are considered as a subclass of molecular sieves. Non-zeolitic molecular sieves are crystalline framework materials in which Si and/or Al tetrahedral atoms of a zeolite lattice are entirely or in part substituted by other I atoms such as B, Ga, Ge, Ti, V, Fe, or P.

Zeolite frameworks are usually negatively charged due to the replacement of $Si^{4+}$ by $Al^{3+}$. In natural zeolites this charge is compensated by alkali or alkali earth cations such as $Na^+$, $K^+$ or $Ca^{2+}$. In synthetic zeolites the charge can also be balanced by quaternary ammonium cations or protons. Synthetic zeolites and molecular sieves are prepared usually under hydrothermal conditions from aluminosilicate or phosphate gels. Their crystallization, according to the hereafter discussed prior art, is accomplished through prolonged reaction in an autoclave for 1–50 days and, often times, in the presence of structure directing agents (templates). The proper selection of template is of extreme importance for the preparation of a particular framework and pore network. A large variety of organic molecules or assemblies of organic molecules with one or more functional groups are known in the prior art to give more than 85 different molecular sieve framework structures. (Meier et al., *Atlas of Zeolite Structure Types*, Butterworth, London, 1992). Excellent up to date reviews of the use of various organic templates and their corresponding structures, as well as the mechanism of structure directing are given in Barrer et al., *Zeolites*, vol. 1, 130–140 (1981); Lok et al., *Zeolites*, vol. 3, 282–291 (1983); Davis et al., *Chem. Mater.*, vol. 4, 756–768 (1992) and Gies et al., *Zeolites*, vol. 12, 42–49 (1992). For example, U.S. Pat. No. 3,702,886 teaches that crystallization of aluminosilicate gel (high Si/Al ratio) in the presence of quaternary tetrapropyl ammonium hydroxide template affords zeolite ZSM-5. Other publications teaching the use of various organic directing agents include, for example, U.S. Pat. No. 3,709,979, wherein quaternary cations, such as tetrabutyl ammonium or tetrabutyl phosphonium, are used to crystallize zeolite ZSM-11 and U.S. Pat. No. 4,391,785 demonstrating ZSM-12 preparation in the presence of tetraethyl ammonium cations. Another zeolite-ZSM-23 synthesis, directed by $(CH_3)_3N^+(CH_2)_7N^+(CH_3)_3$ dications, is taught in U.S. Pat. No. 4,619,820. The use of yet another dicationic template-N, N, N, N', N', N', -hexamethyl-8,11-[4.3.3.0] dodecane diammonium diiodide, for the preparation of zeolite SSZ-26, is shown in U.S. Pat. No. 4,910,006.

Other prior art teaches that primary amines such as propylamine, i - propylamine (U.S. Pat. No. 4,151,189), and diamines, such as diaminopentane, diaminohexane and diaminododecane (U.S. Pat. No. 4,108,881) also direct the synthesis of the ZSM-5 type structure. However, as pointed out by Hearmon et al., *Zeolites*, vol. 10, 608–611 (1990), it is the protonated form of these amines which most likely is responsible for the framework assembly.

In summary, most of the prior art zeolites and molecular sieve frameworks were assembled by using quaternary ammonium cations or protonated forms of amines or diamines as templates.

The search for new organic directing agents, as evident in the increasing number of prior art reports, is attributable to: (i) the need for new and attractive types of stable frameworks and (ii) to the need for expanding the uniform micropore size to mesopore region and thus allowing one to adsorb, process and discriminate among much larger molecules. However, the prior art molecular sieves typically possess uniform pore size in the microporous region. This pore size is predetermined by the thermodynamically favored formation of framework windows containing 8, 10 and 12 - I atom rings. Thus, the ability of the prior art zeolites and molecular sieves to adsorb, process and discriminate among molecules of certain shape and size is strictly limited by the size of these windows. During the last three decades considerable synthetic effort has been devoted to developing frameworks with pore sizes larger than that of the naturally occurring zeolite faujasite (pore size 7.4 Å). However, due to the above limitations, the synthetic faujasite analogs, zeolite X or Y, with 8 Å pore windows (Breck D. W., *Zeolite Molecular Sieves: Structure, Chemistry and Use*; Wiley and Sons; London, 1974), maintained for decades their position as the largest pore molecular sieves. The replacement of aluminosilicate gels by alumino-and gallophosphate gels gave new direction to the synthesis of large uniform pore materials. Thus, a 18-membered ring aluminophosphate molecular sieve VPI-5 (Davis et al., *Nature*, vol. 331, 698–699 (1988)), was found to possess a structure with an hexagonal arrangement of one-dimensional channels (pores) of diameter ≈12 Å. The discovery of a 20-membered ring gallophosphate molecular sieve-cloverite, exhibiting a uniform pore size of 13 Å is disclosed in Estermann M. et al., *Nature*, vol. 352, 320–323 (1991). Recently, Thomas et al., *J. Chem. Soc., Chem. Commun.*, 875–876 (1992) reported a triethyl ammonium cation—directed synthesis of a novel 20-membered ring aluminophosphate molecular sieve, denoted JDF-20, having uniform pore size of 14.5 Å (calculated from lattice parameters). Very recently, a preparation of vanadium phosphate with 18.4 Å lattice cavity was disclosed in Soghmonian et al., *Angew. Chem., Int. Ed. Engl.*, vol. 32, 610–611 (1993). However, the actual pore size of these two materials is unknown since sorption data are lacking. In summary, in spite of the significant progress made toward the preparation of large pore size materials, all of the above mentioned molecular sieves still possess uniform pore size in the microporous region.

A breakthrough toward the preparation of mesoporous molecular sieves have been disclosed recently in U. S. Pat. Nos. 5,098,684 and 5,102,643. The claimed class of mesoporous materials (denoted as M41S) of this prior art was found to possess uniform and adjustable pore size in the range of 13–100 Å. In addition, these materials exhibited a small framework wall thickness of from 8 to 12 Å and elementary particle size of usually much above 500 Å. Depending on preparation conditions M41S materials with hexagonal (MCM-41), cubic (MCM-48) or layered crystallographic structure have been disclosed (Beck et al., *J. Am. Chem. Soc.*, vol. 114, 10834–10843 (1992). The postulated mechanism of formation of these materials involves strong electrostatic interactions and ion pairing between quaternary ammonium liquid crystal cations, as structure directing agents, and anionic silicate oligomer species (U.S. Pat. No. 5,098,684). Related mesoporous structures also have been prepared by rearrangement of a layered silicate (kanemite) (Inagaki et al., *J. Chem. Soc. Chem. Commun.*, vol. 8, 680–682 (1993)) in the presence of quaternary ammonium cations. Recently, Stucky et al. (*Nature*, vol. 368, 317–321 (1994)) extended the electrostatic assembly approach by proposing four complementary synthesis pathways. Pathway 1 involved the direct co-condensation of anionic inorganic species (I) with a cationic surfactant ($S^+$) to give assembled ion pairs ($S^+I^-$), the original synthesis of MCM-41 being the prime example (U.S. Pat. No. 5,098,684). In the charge reversed situation (Pathway 2) an anionic template ($S^-$) was used to direct the self-assembly of cationic inorganic species (I+) via $S^-I^+$ ion pairs. The pathway 2 has been found to give a hexagonal iron and lead oxide and different lamellar lead and aluminum oxide phases (Stucky et al., ibid). Pathways 3 and 4 involved counterion ($X^-$ or $M^+$) mediated assemblies of surfactants and inorganic species of similar charge. These counterion-mediated pathways afforded assembled solution species of type $S^+X^{-I+}$ (e. g., $X^-=Cl^-$, $Br^-$) or, $S^-M^+I^-$ (e. g., $M^+=Na^+$, $K^+$), respectively. The viability of Pathway 3 was demonstrated by the synthesis of a hexagonal MCM-41 using a quaternary ammonium cation template and strongly acidic conditions (5–10 M HCl or HBr) in order to generate and assemble positively - charged framework precursors (Stucky et al., ibid). In another example, a condensation of anionic aluminate species was accomplished by alkali cation mediated ($Na^+$, $K^+$) ion pairing with an anionic template ($C_{12}H_{25}OPO_3^-$). The preparation of the corresponding lamellar Al $(OH)_3$ phase in this case has been attributed to the fourth pathway ($S^-M^+I^-$). Also, we have reported (Pinnavaia et al., *Nature*, vol. 368, 321–323 (1994)) the preparation of a mesoporous silica molecular sieve and a Ti-substituted analogue by the acid catalyzed hydrolysis of inorganic alkoxide precursors in the presence of primary ammonium ions produced by the acid.

Since all of the above pathways are based on charge matching between ionic organic directing agents and ionic inorganic reagents, the template is strongly bonded to the charged framework and difficult to recover. In the original Mobil approach (U.S. Pat. No. 5,098,684) the template was not recovered, but simply burned off by calcination at elevated temperatures. Recently, it has been demonstrated that the ionic surfactant in Pathway 1 materials could be removed by ion-exchange with acidic cation donor solution (U.S. Pat. No. 5,143,879). Also, the template—halide ion pairs in the framework of acidic Pathway 3 materials were displaced by ethanol extraction (Stucky et al., ibid). Thus, ionic template recovery is possible, provided that exchange ions or ion pairs are present in the extraction process.

While water molecules are easily removed by heating and evacuation, the quaternary ammonium cations, due to their high charge density, are strongly bonded or confined to the pore cavities and channels of the negatively charged framework. The same concepts are expected to apply for the charge reversed situation were an anionic template is confined in the pores of a positively-charged framework. Therefore, a cation or anion donor or ion pairs are necessary in order to remove the charged template from the framework of the prior art molecular sieves.

Textural porosity is the porosity that can be attributed to voids and channels between elementary particles or aggregates of such particles (grains). Each of these elementary particles in the case of molecular sieves is composed of certain number of framework unit cells or framework-confined pores. The textural porosity is usually formed in the stages of crystal growth and segregation or subsequent thermal treatment or by acid leaching. The size of the textural pores is determined by the size, shape and the number of interfacial contacts of these particles or aggregates. Thus, the size of the textural pores is usually at least one or two orders of magnitude larger than that of the framework-confined pores. For example, the smaller the particle size, the larger the number of particle contacts, the smaller the textural pore size and vice versa. One skilled in the art of transmission electron microscopy (TEM) can determine the existence of framework-confined micropores from High Resolution TEM (HRTEM) images or that of framework-confined mesopores from TEM images obtained by observing microtomed thin sections of the material as taught in U.S. Pat. No. 5,102,643.

One skilled in the art of adsorption could easily distinguish and evaluate framework-confined uniform micropores by their specific adsorption behavior. Such materials usually give a Langmuir type (Type I) adsorption isotherm without a hysteresis loop (Sing et al., *Pure Appl. Chem.*, vol. 57, 603–619 (1985)). The existence of textural mesoporosity can easily be determined by one skilled in the art of SEM, TEM and adsorption. The particle shape and size can readily be established by SEM and TEM and preliminary information concerning textural porosity can also be derived. The most convenient way to detect and assess textural mesoporosity is to analyze the $N_2$ or $Ar_2$ adsorption-desorption isotherm of the solid material. Thus, the existence of textural mesoporosity is usually evidenced by the presence of a Type IV adsorption-desorption isotherm exhibiting well defined hysteresis loop in the region of relative pressures Pi/Po>0.4 (Sing et al., *Pure Appl. Chem.*, vol. 57, 603–619 (1985)). This type of adsorption behavior is quite common for a large variety of paracrystalline materials and pillared layered solids.

The microporous zeolites and molecular sieves of the prior art exhibit mainly framework-confined uniform micropores, and no textural mesoporosity as evidenced by their Langmuir type adsorption isotherms without hysteresis loops at Pi/Po>0.4 and the large crystalline aggregate size of >2 $\mu$m, more usually from 5 to 20 $\mu$m. The typical values for their specific surface area are from 300–800 $m^2$/g and for the total pore volume ≤0.6 $cm^3$/g (*Perspectives in Molecular Sieve Science*, Eds. Flank, W. H. and White T. E. Jr., ACS symposium series No. 368, Washington D. C., p. 247; 524; 544 (1988)). Most of these structures are prepared by prolonged crystallization at hydrothermal conditions, using quaternary ammonium cations or protonated primary, secondary or tertiary amines to assemble the anionic inorganic species into a framework. It should also be noted that the use in the prior art of neutral amines and alcohols as templates (Gunnawardane et al., *Zeolites*, vol. 8, 127–131 (1988)) has led to the preparation of only microporous highly crystalline (particle size >2$\mu$m) molecular sieves that lack appreciable textural mesoporosity. For the mesoporous molecular sieves of the MCM-41 family the uniform mesopores are also framework-confined. This has been verified by TEM lattice images of MCM-41 shown in U.S. Pat. No. 5,102,643. Therefore, the framework of this class of materials can be viewed as an expanded version of a hexagonal microporous framework. The existence of these framework-confined uniform mesopores was also confirmed by the capillary condensation phenomenon observed in their adsorption isotherms. A typical $N_2$ adsorption-desorption isotherm of MCM-41 is shown in Davis et al., *XIII North American Meeting of the Catalysis Soc., Book of Abstracts*, p. D14 (1993). This adsorption isotherm is essentially the same as that obtained previously by Sing et al., *J. Chem. Soc., Chem. Commun.*, 1257–1258 (1993). The isotherm is constituted by sharp adsorption uptake followed by a hysteresis loop in the Pi/Po region of 0.3 to 0.4. This hysteresis corresponds to capillary condensation into the framework-confined uniform mesopores. The lack of appreciable hysteresis beyond Pi/Po >0.4 implies the absence of textural mesoporosity. This lack of textural mesoporosity is also supported in some cases by the highly ordered hexagonal prismatic shaped aggregates of size >2 $\mu$m (Beck et al., *J. Am. Chem. Soc.*, vol. 114, 10834–10843 (1992). The total pore volume of the material reported by Davis et al. is ≈0.7 $cm^3$/g and that of the framework-confined mesopores, as determined from the upper inflection point of that hysteresis loop, is almost equal to that of the total pore volume. Therefore, the ratio of textural to framework-confined mesoporosity here approaches zero. The size of the framework-confined uniform mesopores is ≈30 Å.

In summary, the crystalline molecular sieve materials of the aforementioned prior art typically lack appreciable textural mesoporosity. However, there is increasing number of reports in the literature suggesting that textural mesopores behave as a transport pores to the framework-confined uniform pores and that they greatly improve the access and the performance of adsorbents, ion-exchangers and catalysts. This, for example, is demonstrated in Pinnavaia et al., *Nature*, vol. 368, 321–323 (1994); Chavin et al., *J. Catal.*, vol. 111, 94–105 (1988) and in Cartlidge et al., *Zeolites*, vol. 9, 346–349 (1989). According to this prior art, the transport pores provide more efficient assess to the framework-confined pores of the zeolite.

In summary, the prior art molecular sieve materials, as well as their preparation approaches have the following disadvantages:

1. The prior art uses charged surfactant ions ($S^+$ or $S^-$) as templates in order to assemble an inorganic oxide framework from charged inorganic precursors ($I^-$ or $I^+$). These charged templates are usually expensive, strongly bonded to the charged inorganic oxide framework and difficult to recover. In addition, some charged templates, such as quaternary ammonium ions are highly toxic and, therefore, potential health hazards. In all the prior art examples the electrostatically bonded templates were removed from the framework by either a burning off process or by an ion-exchange reaction with an ion donor solution. Also, ion pairs were necessary in order to extract the template from the framework of pathway 3 materials.

2. Yet other important disadvantages of the prior art mesoporous molecular sieves are the small framework wall thickness (from 8 to 12 Å), large elementary particle size (typically much above 500 Å) and the absence of an optimal balance of framework-confined and textural mesoporosity. This deficiency is attributable to the strong electrostatic interactions and the specific preparation conditions governing their self-assembly process. This does not contribute to improving the thermal stability, the textural mesoporosity and to accessing the framework-confined uniform mesopores. The lack of textural mesoporosity could lead to serious diffusion limitations in many potential applications. The ratio of textural to the framework-confined mesoporosity of these materials is usually close to zero.

The aforementioned disadvantages of this prior art severely limit the practical use of these crystalline materials.

Therefore, there is a need for new, templated, crystalline inorganic oxides with regular wormhole like channels. Also there is a need for a new method for the preparation of these mesostructures which would allow for cost reduction by employing relatively expensive reagents and mild reaction conditions while at the same time providing for the effective recovery and recyclability of the template.

SUMMARY OF THE INVENTION

The present invention relates to a quasi crystalline inorganic oxide composition having framework-confined mesopores prepared by a method which comprises reacting a neutral amine template and a neutral inorganic oxide precursor wherein the template is dissolved in a solution of water and a water miscible organic solvent containing a larger volume of either the alkanol or the water, aging of the precipitate and removal of at least some of the template and the aqueous solution to form the quasi crystalline composition which has regular wormhole shaped channels.

Further, the present invention relates to a method for the preparation of a synthetic, quasi crystalline inorganic oxide composition which comprises: (a) preparing a first solution of a neutral inorganic oxide precursor; (b) preparing a second solution of a neutral amine template in water and a water miscible organic solvent by stirring it at a temperature between about minus 200° and plus 1000° C., wherein the solutions together contain a volume excess of the water or the alkanol; (c) mixing of the solutions of steps (a) and (b) at a temperature between about minus 20° and plus 100° C. to form a precipitate which is aged to form the quasi crystalline inorganic oxide composition; (d) separating at least some of the template from the crystalline composition; and (e) optionally calcining the quasi crystalline composition.

OBJECTS

An object of the present invention is to provide novel quasi crystalline, inorganic oxide compositions with regular wormhole shaped channels.

Another object of the present invention is to provide inexpensive preparation methods for these materials which avoid the use of charged ionic templates and charged inorganic oxide precursors and high temperature hydrothermal synthesis conditions.

Still another object of this invention is to provide for the facile recovery and recycling of the template by new separation art involving simple solvent extraction from the quasi crystalline inorganic oxide composition.

These and other objects will become increasingly apparent from the following description and the drawings.

BRIEF DESCRIPTION OF THE DRAWINGS

FIG. 4A shows mesoscale fundamental particles and fractal-like texture obtained from water-rich solution; FIG. 4B shows the spheroid fundamental particles and macroscale beads-on-a-string texture obtained from ethanol-rich solution. FIGS. 4C and 4D show the wormhole-like framework pores obtained from water-rich solution.

FIG. 5A is a low magnification image showing the retention of the textural mesopores and FIG. 5B is a high magnification image showing the absence of framework pores.

DESCRIPTION OF PREFERRED EMBODIMENTS

Figure 1:
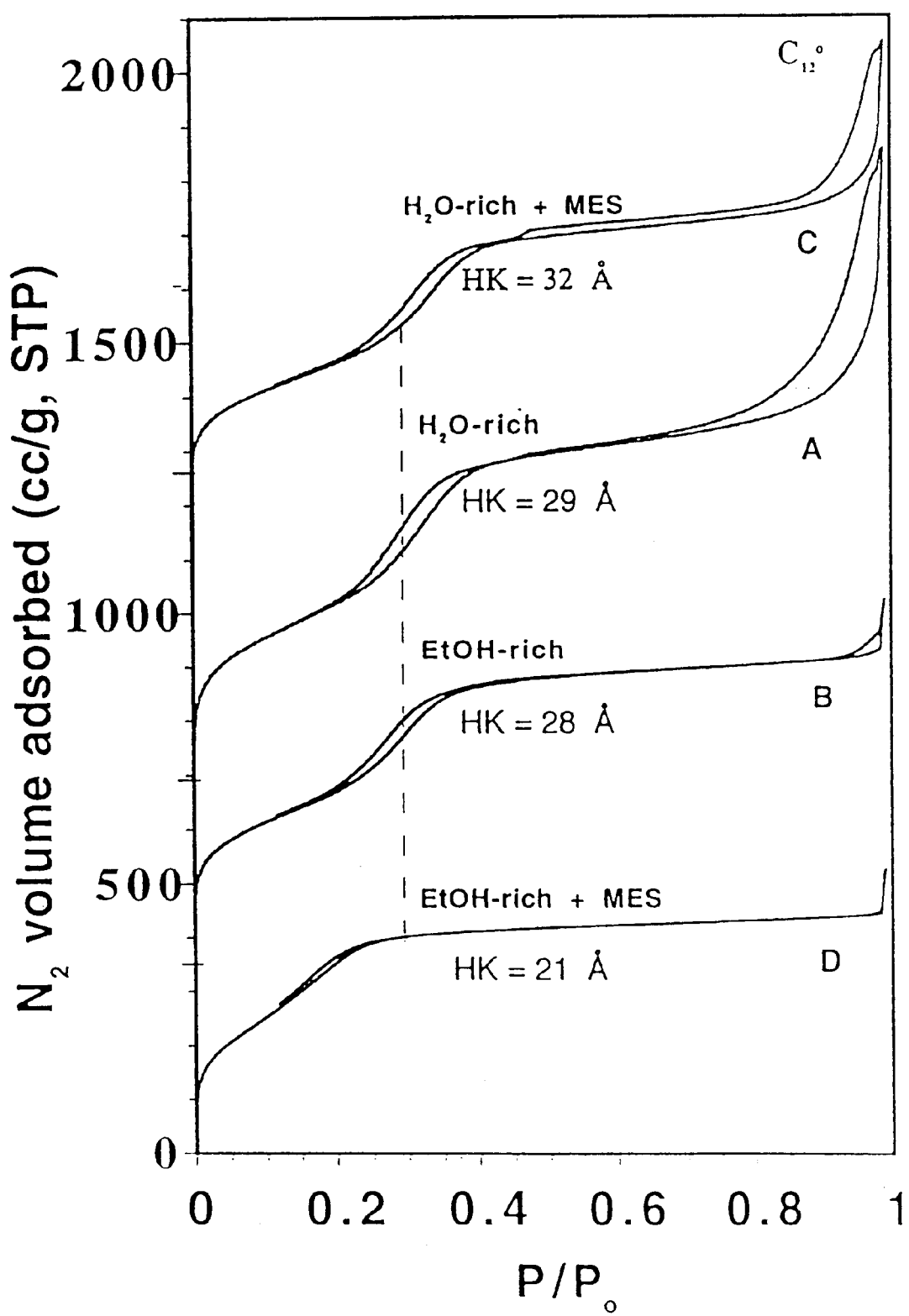
FIG. 1 is a graph showing $N_2$ adsorption-desorption isotherms for the silicas assembled at ambient temperatures from dodecylamine and tetraethyl orthosilicate (TEOS) : Curves A and B are for derivatives obtained from a water-rich solution (water:ethanol=90:10 (v/v)) and ethanol-rich solution (water:ethanol=35:65 (v/v)) and curves C and D are for derivatives prepared from the same water-rich and ethanol-rich solutions, but in the presence of mesitylene (Mes/S°=of 1.0). The HK values are the Horvath-Kawazoe pore diameters.

The present invention relates to a quasi crystalline inorganic oxide composition with regular wormhole shaped channels. The templating mechanism comprises reacting a neutral amine template solution containing water a miscible organic solvent, preferably an alkanol containing 1 to 10 carbon atoms, with an excess of one or the other and a neutral inorganic oxide precursor solution to form a reaction product, hydrolysis of the reaction product, and the subsequent removal of the aqueous solution and the template.

The framework-confined uniform pores are pores formed by nucleation and assembly of the framework elementary particles. These pores typically are cavities and channels confined by the solid framework.

The size of the cavities and channels, i.e. the size of the framework-confined uniform pores, in molecular sieve materials is predetermined by the thermodynamically favored assembly routes. The framework-confined pores of freshly crystallized product are usually occupied by the template, water and alkanol molecules.

The quasi crystalline inorganic oxide compositions of the present invention are obtained by a new neutral preparative method. The formation of the mesoporous structures is accomplished primarily by H-bonding between a neutral template and a neutral inorganic oxide precursors, followed by further hydrolysis and crosslinking of $IO_m$ units, where I is a central metallic or non-metallic element coordinated to m oxygen atoms (2<m<8). Specifically, the said method comprises the formation of a precipitate by mixing of a neutral template solution with a neutral inorganic oxide precursor, preferably a inorganic alkoxide or a neutral inorganic oxide sol, in the presence of a molar excess amount over the inorganic oxide of water and alkanol, preferably ethanol or methanol. Much of the template can be recovered by extraction of the templated product with water or with ethanol, or a mixture thereof, or by vacuum distillation. Preferably, the template is removed by extraction with ethanol. Complete removal of the last traces of template and the further crosslinking of the IO$_m$ framework is accomplished by calcination at 300° to 1000° C.

Hydrogen bonding between the template and the reagent is the primary driving force of the framework assembly process of this invention. The neutral amine plays the role of both a solvent and template for the neutral precursor. Water plays a role of hydrolyzing reagent and the alcohol acts as co - solvent.

The template solution is preferably augmented with an additional structure directing agent. This is an organic compound which is essentially insoluble in water, but soluble in the miscible organic solvent. The preferred compounds are non-polar.

The molar ratio of amine to inorganic oxide precursor in the initial reaction mixture is between about 0.05 and 3, preferably about 0.05 and about 1.4. The crystalline inorganic oxide composition of the present invention preferably has in its as - synthesized and anhydrous state the following formula:

$$A_xSi_yO_z$$

wherein A is selected from the group consisting of Ca, Mg, Zn, Cu, B, Al, Ga, Cr, Fe, Ge, Ti, V, Zr, V, Sn, W and Mo, x is between 0 to 1.0, y is between about 0 and 1.0 and z is between about 1.0 and 3.0 and the sum of x +y is equal to 1.0.

The quasi crystalline mesoporous materials of this invention may be characterized as formed by H-bonding between neutral inorganic oxide precursors containing I–OH groups as hydrogen donors and a neutral amine templates as hydrogen acceptors, followed by further hydrolysis and crosslinking of IO$_m$ units under mild reaction conditions. Specifically, the method comprises formation of a precipitate by mixing of a neutral amine template solution with a solution of at least one inorganic oxide precursor, preferably an inorganic alkoxide, or a neutral inorganic oxide sol or gel precursor in the presence of a water and alkanol with an excess of either the water or the alkanol, followed by hydrolysis and aging under stirring at temperature of at least minus 20° C. for at least 0.5 h.

The compositions can be used as an adsorbents, ion-exchangers or a catalysts. According to this invention, the removal of the template from the reaction product can be achieved by at least four ways: (i) air drying followed by calcination in air or in inert gas at temperature from 300–1000° C. for 30 min to 72 h; (ii) solvent extraction of the templated product; and (iii) by vacuum distillation of the product; (iv) by various combinations of (i) to (iii). The fact that the template can be recycled by non-ionic recovery methods (ii) and (iii) is also a distinctive feature of this invention. Procedure (i) results in the destruction of the template. The separation of the template by extraction or distillation should be followed by air drying and calcination in air or inert gas to remove the final traces of template and to complete the crosslinking of the mesostructure.

After template removal and calcination, the said material can be used as an adsorbent for non-polar or polar organic molecules or as a gas drying agent. Furthermore, the said calcined product when framework substituted, or subsequently impregnated, as taught in Sachtler, W. M. H., Catal. Today 15, 419–429 (1992), with proper amount of catalytically active element, such as Al, Ti, V, Pt, Pd, Cu, Cr or mixture thereof, or when functionalized with metal salts or organometallic compounds could be used as a catalyst for cracking, hydrocracking, hydrogenation-dehydrogenation, isomerization, polymerization or redox reactions involving organic substrates.

The new preparation method of the composition of this invention involves the preparation of solutions comprising sources of di-, tri-, tetra-, penta- or hexavalent elements, or mixture thereof, a solvent (optional), aging and reacting this solution with template solution at mild reaction conditions, under stirring, until formation of the desired crystalline product and recovering the crystalline material. The template, can be described more particularly as a neutral (non-ionic) molecule of formula $R_1R_2R_3N$, wherein N is nitrogen and at least one of $R_1$, $R_2$ and $R_3$ is selected from the group of alkyl of from 6 to 22 carbon atoms or aryl of from 6 to 18 carbon atoms or combination thereof. The remaining R groups are selected from the group consisting of hydrogen or alkyl from 1 to 22 carbon atoms or combination thereof.

The preparation procedures of the compositions comprise steps as follows:

(i) preparing a solution of neutral inorganic oxide precursor, preferably an inorganic alkoxide of a di-, tri-, tetra-, penta- or hexavalent element or mixture thereof in the presence (optional) of hydrolyzing agent and/or co-solvent in a molar excess of one or the other;

(ii) preparing a solution of the neutral template in a water and ethanol with a molar excess of the alkanol or the water;

(iii) reacting the inorganic oxide precursor solution with the template solution by stirring at a temperature from minus 20° C. to plus 100° C. to produce a precipitate;

(iv) air drying the precipitate and/or separating the template by either extraction with water or alcohol or a mixture thereof, or by distillation of the templated product. After template removal, the composition is subjected to calcination to remove trace amounts of template and to complete the crosslinking of the framework; and (v) Calcining the product at 300 to 1000° C. in air or inert gas for at least 30 min.

The inorganic oxide solutions are prepared from neutral precursors such as the silicates of Ser. No. 08/293,806, filed Aug. 22, 1994 and such as alkoxides, inorganic hydrocarbons such as silanes, or inorganic complexes which upon hydrolysis afford a I-OH species. The list of preferred alkoxides include, in particular, aluminum(III) tri-ethoxide, aluminum(III) isopropoxide, aluminum(III) n-, tert - or sec-butoxide, antimony(III) isopropoxide, antimony(III) n-butoxide, calcium(II) ethoxide, calcium(II) isopropoxide, calcium(II) tert- butoxide, chromium(IV) tert-butoxide, chromium(III) isopropoxide, copper(II) methoxyethoxide, gallium(III) isopropoxide, germanium(IV) ethoxide, germanium(IV) isopropoxide, indium(III) isopropoxide, iron(III) ethoxide, iron(III) tert - butoxide, iron(III) isopropoxide, lead(II) isopropoxide, lead(II) tert - butoxide, magnesium(II) ethoxide, molybdenum (V) isopropoxide, manganese (II) isopropoxide, niobium(V) ethoxide, strontium(II) isopropoxide, tetramethyl orthosilicate, tetraethyl orthosilicate (TEOS), tetrapropyl orthosilicate, tetrabutyl orthosilicate, tetrahexyl orthosilicate, H[OSi(OC$_2$H$_5$)$_2$]OH where n=4–6, RSi(OR)$_3$, tin(IV) isopropoxide, tetraethyl orthotitanate, tetrapropyl orthotitanate, tetraisopropyl orthotitanate (TIPOT), tetrabutyl orthotitanate, tetraoctadecyl orthotitanate, tungsten(VI) ethoxide, tungsten(VI) isopropoxide, vanadium(V) triisopropoxide oxide, zinc(II) isopropoxide, zinc(II) tert-butoxide, zirconium(IV) n-propoxide, zirconium(IV) isopropoxide, zirconium(IV) tert- butoxide or mixtures thereof. Also, a variety of a neutral colloidal inorganic oxide precursor solutions or inorganic oxide gels also can be used to prepare the compositions of the present invention. For example, a potential source of a neutral silica include the variety of commercially available fumed silicas or silica gels.

The co-solvent is selected from the group of normal or isomerized alcohols having 1 to 12 carbon atoms and at least one OH group, such as methanol, ethanol, propanol, butanol, hexanol, octanol, dodecanol. More preferably, said co-solvent is methanol, ethanol, propanol, 2-propanol or mixture thereof. Those skilled in the art will know that polyols in which more than one OH group is present also can be used as a co-solvent.

The reacting of the inorganic oxide precursor solution and template solution is preferably carried out at 20 to 75° C. by random order of reagent addition, preferably by adding the inorganic oxide precursor solution to the stirred template solution. More specifically, said reacting is performed by H-bonding between neutral inorganic oxide precursors and a neutral template, followed by further hydrolysis and crosslinking of $IO_m$ units at mild reaction conditions. This H-bonding most likely occurs generally between any I–OH or I-proton donor compound and the lone pair of electrons on the central atom of the head group of the organic template.

The calcinating is performed by heating in an oven at a temperature preferably from 300–650° C. for 4 h.

The outstanding features of the present method are:

(i) The use of neutral templates, particularly amines or diamines, in an alkanol, preferably methanol or ethanol, and water with a volume excess of one or the other to assemble the mesoporous framework structure;

The templated inorganic oxide compositions of the present invention can be combined with other zeolites or clays or inorganic oxides or organic polymers or mixture thereof, in order to prepare adsorbents, ion-exchangers, catalysts, catalytic carriers or composite membranes with high thermal and mechanical resistance. In addition, one skilled in the art can impregnate the composition of the present invention or use it as an encapsulating agent for transition metal macrocycles such as phthalocyanines and porphyrins. The active phase in these cases could be a transition metal for example Cu, Co, Ni, Fe, Ti, V, W, Pt, Pd or Mo or mixtures thereof. These catalysts can be used in conversion such as catalytic cracking, hydrocracking, reforming, isomerization, dealkylation or oxidation in the presence or absence of $H_2O_2$ or $O_2$ or mixture thereof.

The following specific examples are intended to be illustrative of the present invention, but are not intended to limit the invention. Water:ethanol solvent mixtures of differing polarity have been used to tailor the framework and textural mesopores of silica molecular sieves through an electrically neutral ($S°I°$) assembly pathway ($S°$=dodecyl or tetradecylamine; $I°$=tetraethyl orthosilicate). Mesostructure assembly from a water-rich solvent mixture, water:ethanol =90:10 (v/v), afforded wormhole-like channels with a complementary textural pore volume equal in magnitude to the framework pore volume. An ethanol-rich mixture, water:ethanol =35:65 (v/v) also formed wormhole-like channels, but the textural porosity was less than 20% of the framework pore volume. Mesostructured derivatives with high textural porosity were comprised of mesoscale fundamental particles with a fractal-like surface and aggregate into larger particles with low mass fractal dimensions. In contrast, mesostructures with low textural porosity were assembled into much larger aggregates of macroscale spheroid to disk-shaped fundamental particles. The differences in particle textures were attributed to differences in $I°$ hydrolysis rates and $S°I°$ nucleation and growth rates in the two solvent systems. The presence of mesitylene and other hydrophobic organic molecules in the reaction mixtures resulted in an expansion of the framework pores under water-rich conditions. Pore contraction, however, was observed with mesitylene present under ethanol-rich conditions. This versatile structure-modifying property of mesitylene in $S°I°$ assembly is explained by the solvent-dependent binding of the aromatic molecules to two structurally distinct and size-altering "dissolved" and "adsorbed" states at the centers and interfacial surfaces of the surfactant micelle, respectively. Thus, both the framework and textural pores of the silica can be readily tailored to the needs of a particular materials application through $S°I°$ assembly by a judicious choice of an appropriate solvent and an auxiliary structure modifier.

Although they are distinguishable with regard to structural ordering, MCM-41 and the molecular sieves of the present invention both exhibit a sharp step in their nitrogen adsorption isotherms, corresponding to the presence of a regular mesoporous framework. Owing to the very small elementary particle size of many mesostructured derivatives, they can exhibit complementary textural mesopores, in addition to framework pores. The textural pore volumes can be up to 1.5 or more times as large as the framework pore volumes, whereas MCM-41 exhibits very little textural mesoporosity (Schmidt, R. E., et al., J. Am Chem. Soc. 117; 4049 (1995)). The textural mesopores are important because they greatly facilitate mass transport to the framework mesopores.

Another potential benefit of $S°I°$ assembly is the possibility of conducting mesostructure synthesis in media of diverse polarity. Unlike their ionic counterparts, $S°$ and $I°$ reagents are generally soluble in a wide range of solvents. Thus, salvation effects on the rates of hydrolysis and assembly might be an effective means of controlling structure. One of the objectives of the present invention is to show tailoring of both the framework and the textural mesopores of the mesostructured molecular sieves by controlling the polarity of the reaction medium in which the assembly process is carried out. The present invention makes use of water:alkanol compositions to control solvent polarity, textural porosity and framework porosity.

The role of mesitylene as an auxiliary structure-directing agent was investigated in both water-rich and alkanol-rich solvent systems. By using salvation effects to shift the equilibrium between structurally distinct binding states of mesitylene in the surfactant micelles (Mukerjee, P., et al., J. Phys. Chem. 82:1620 (1978); and Gordon, J. E., et al., J. Phys. Chem. 74:957 (1970)), we are able to effect an expansion or contraction of the framework pore structure mesoporosity. The ability to control both framework and textural mesoporosity can be of great value in designing mesostructured materials as catalysts, adsorbents and sensor materials.

EXAMPLES 1 to 4

Silica molecular sieves were prepared by $S°I°$ assembly pathways in water:ethanol solvent mixtures of differing composition and polarity. In both reaction media tetraethyl orthosilicate (TEOS) served as the neutral silica precursor and dodecylamine and tetradecylamine were the neutral structure director. In a typical synthesis the surfactant was dissolved in ethanol, and then the desired amount of water was added under vigorous stirring to obtain a homogeneous solution. TEOS was added to the surfactant solution and the mixture was allowed to react under stirring at ambient temperature for about 20 hours. The reactions were carried out in an open beaker in a well ventilated hood to allow for some evaporation of solvent and concentration of the solid reaction products. When mesitylene was used as an auxiliary structure director, it was added to the surfactant solution and stirred for 15 minutes before the addition of TEOS. All of the reaction products were filtered, dried in air, and calcined at 650° C. in air for 4 hours.

For the purposes of probing the effect of solvent polarity on textural porosity, it was desirable to form silica molecular sieves from water-rich and ethanol-rich solutions with equivalent framework porosities. To achieve the framework pore structures, we used reagent concentrations in the ethanol-rich system that were twice the concentrations for the water-rich medium. For the silica molecular sieves assembly in the relatively low polarity, ethanol-rich reaction medium, where water:ethanol volume ratio was 35:65, the molar composition of the reaction mixture was 1.0 TEOS:0.25 Surfactant : 18 EtOH : 34$H_2O$. For assembly in a relatively high polarity, water-rich solvent mixture, namely, 90:10 (v/v) water:ethanol, the molar composition was 1.0 TEOS : 0.25 Surfactant : 10 EtOH:130 $H_2O$.

Powder X-ray diffraction patterns were measured using Cu-Kα radiation (λX=1.542 Å and a Rigaku Rotaflex diffractometer equipped with a rotating anode operated at 45 kV and 100 mA. The scattering and receiving slits were ⅙ degree and 0.3 degree, respectively.

$N_2$ adsorption and desorption isotherms at −196° C. were obtained on a Coulter Omnisorp 360CX Sorptometer operated under continuous adsorption mode. Pore size distributions were calculated from the $N_2$ adsorption branch using the Horvath-Kawazoe model (Horvath, G., et al., J. Chem. Eng. Jpn. 16:470 (1983)).

Transmission electron microscopy (TEM) studies were carried out on a JEOL 100CX instrument using an electron beam generated by a $CeB_6$ filament and an acceleration voltage of 120 kv. The resolution of the instrument was about 6 Å, as estimated by indirect measurement of the spherical aberration constant (Spence, J. C. H., "Experimental High-Resolution Electron Microscopy", P264, Oxford University Press, New York (1988)) under medium-high magnification (i.e., 100,000X). Therefore, it was possible to resolve pores above about 30 Å. The specimens were prepared by dipping a carbon coated copper grid into a suspension (0.1 wt%) of mesoporous material in ethanol that was pre-sonicated for 10 minutes. Attempts to use thin-sectioned specimens were abandoned, because thin sectioning caused damage and loss of texture pore information.

Two versions of silica molecular sieves were prepared through S°I° assembly at ambient temperature in reaction media that differed in solvent polarity. In one reaction system the mesostructures were formed from a "water-rich" solution of 90:10 (v/v) water:ethanol. The other reaction medium was a less polar "ethanol-rich" solution of 35:65 (v/v) water:ethanol. Two S°surfactants, namely, dodecylamine and tetradecylamine, were used as structure directors. The reaction stoichiometries were the same for both the water-rich and the ethanol-rich reaction systems (S°/I°= 0.25). When mesitylene (Mes) was present as an auxiliary structure director, the Mes/S° molar ratio was 1.0 or 4.5.

Figure 2:
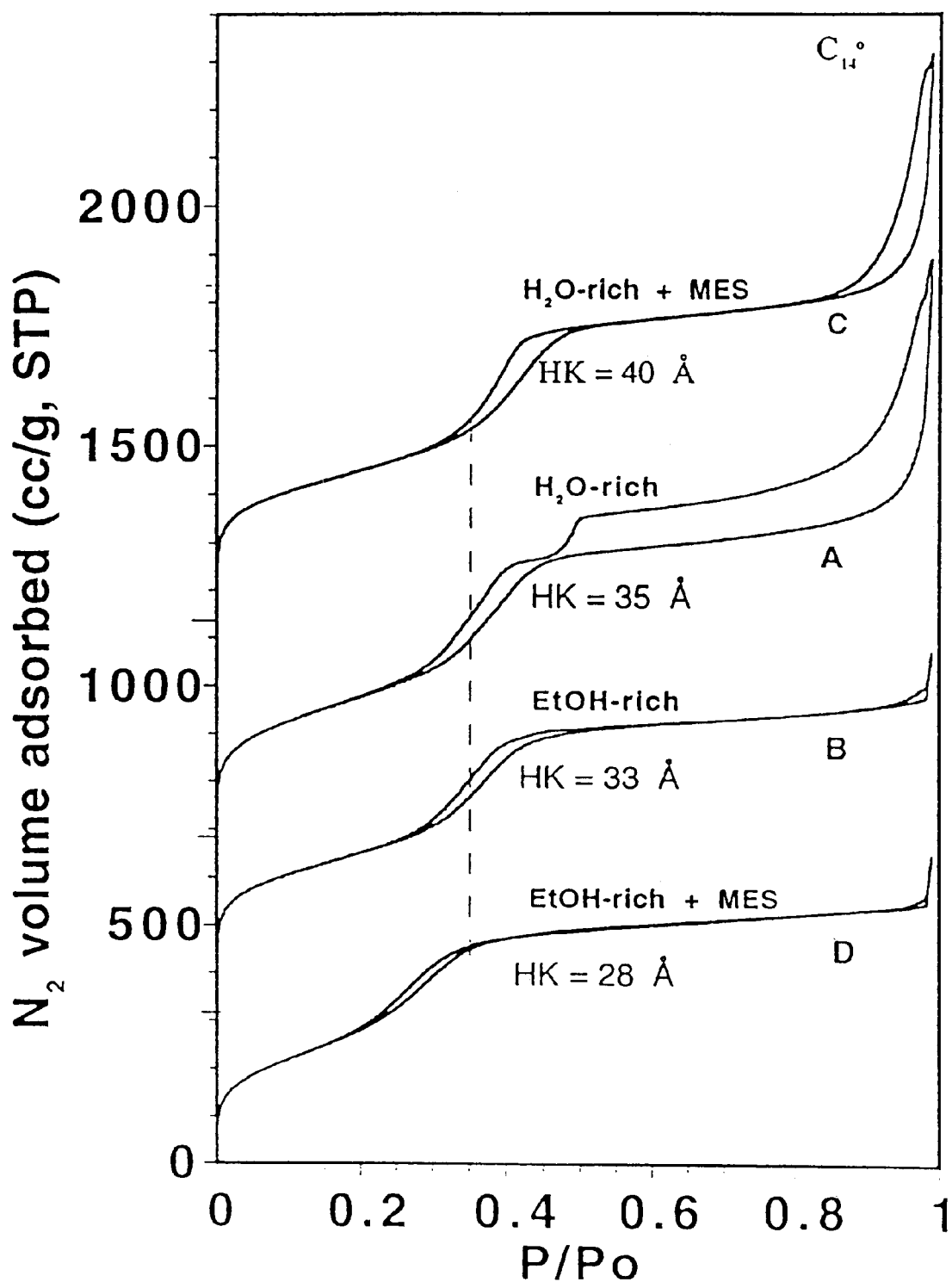
FIG. 2 is a graph showing $N_2$ adsorption-desorption isotherms for the silicas prepared from tetradecylamine and TEOS in water-rich and ethanol-rich solution. The labeling of the isotherms A to D is the same as in FIG. 1.

FIGS. 1 and 2 provide $N_2$ adsorption-desorption isotherms for the silica molecular sieves obtained from dodecylamine and tetradecylamine as structure directors, respectively. The adsorption properties of the mesostructures assembled from the two surfactants under the same reaction conditions are qualitatively equivalent. As can be seen from the isotherms labeled A and B in both Figures, the structures obtained from the water-rich and ethanol-rich solutions give stepped-shaped isotherms at P/Po <0.4. The positions of the steps correspond to Horvath-Kawazoe pore sizes of 28–29 Å(S°=$C_{12}H_{25}NH_2$) and 33–35 Å(S°=$C_{14}H_{29}NH_2$).

Although the mesostructures obtained from the water-rich and ethanol-rich media have equivalent frameworks, the textural mesoporosity, as evidenced by the $N_2$ adsorption/desorption in the partial pressure region P/Po >0.4, depends dramatically on the polarity of the medium used for assembly. A textural pore volume even larger than the framework pore volume can be obtained from the water-rich system, whereas the ethanol-rich medium generates a mesostructure with little or no textural pores. As will be seen from TEM images presented below, the high textural mesoporosity for the water-rich system is associated with the presence of extremely small fundamental particles.

We consider next the effect of mesitylene on the framework pore structure and textural mesoporosity of the silica molecular sieves assembled from water-rich and ethanol-rich solutions. The structure mediating properties of mesitylene is manifested in the adsorption-desorption curves labeled C and D in FIGS. 1 and 2. The presence of mesitylene at Mes/S°=1 in the water-rich systems causes the adsorption step to be significantly shifted to higher relative pressure. The shift in the step position corresponds to a 3–5 Åincrease in HK pore size. In the ethanol-rich medium, however, the presence of mesitylene results in a shift of the step position to lower relative pressures, corresponding to a 5–7 Å decrease in HK pore diameter.

Although mesitylene can substantially expand or contract the framework pores depending on the polarity of the reaction medium, it does not alter the key role of the solvent in regulating the textural porosity. As will be shown below, mesitylene actually increases the textural mesoporosity under water-rich assembly conditions, but it has only a minor influence on the extremely low textural pore volume of the product when assembled under ethanol-rich conditions.

EXAMPLE 5

Figure 3A:
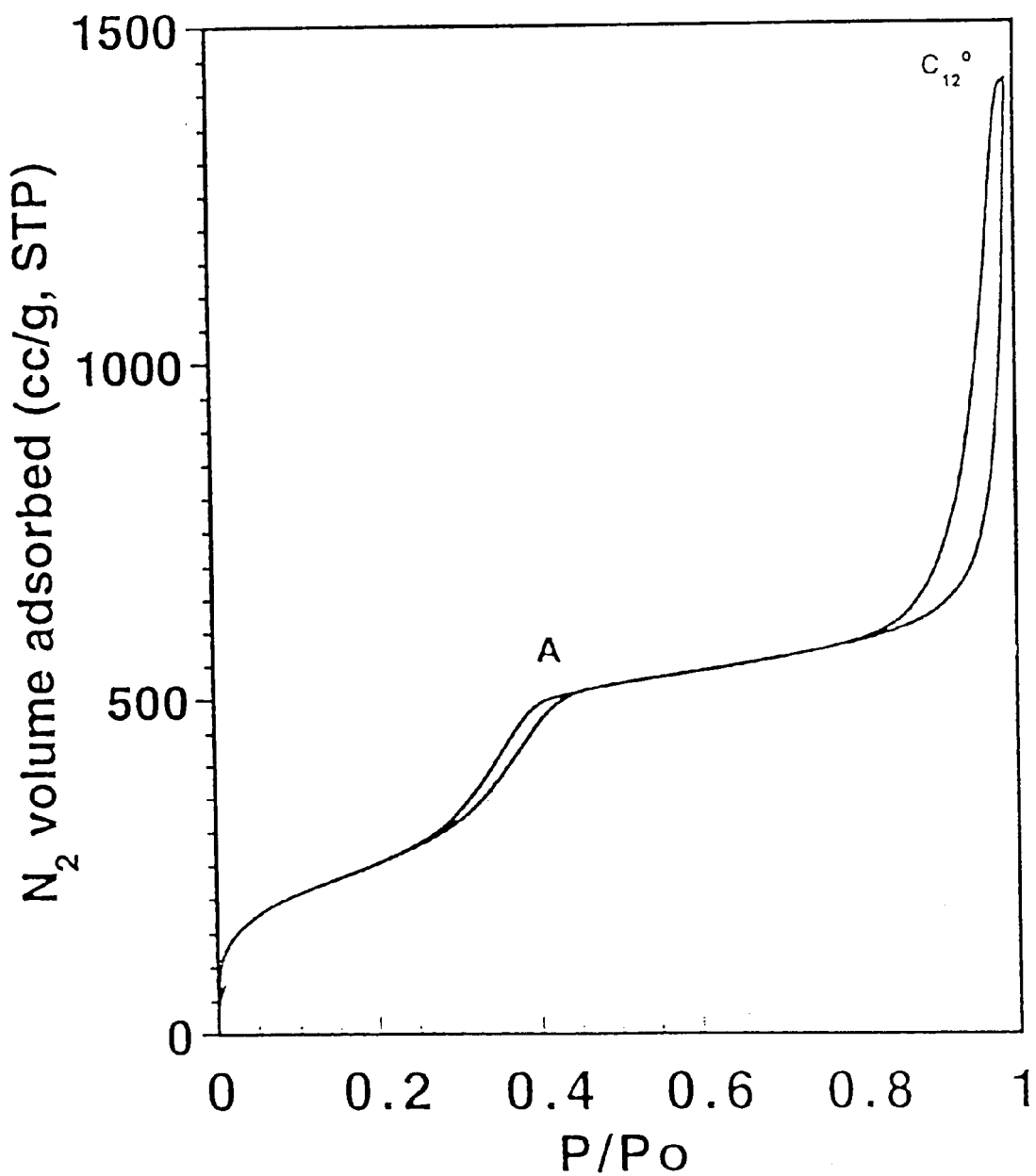
FIGS. 3A and 3B are graphs of $N_2$ adsorption-desorption isotherms for a silica prepared from dodecylamine in water-rich solution in the presence of mesitylene (Mes/S=4.5): (A) after calcination at 650° C. with retention of framework and textural mesopores and (B) after calcination at 1000° C. with collapse of framework pores but with retention of textural pores.
Figure 3B:
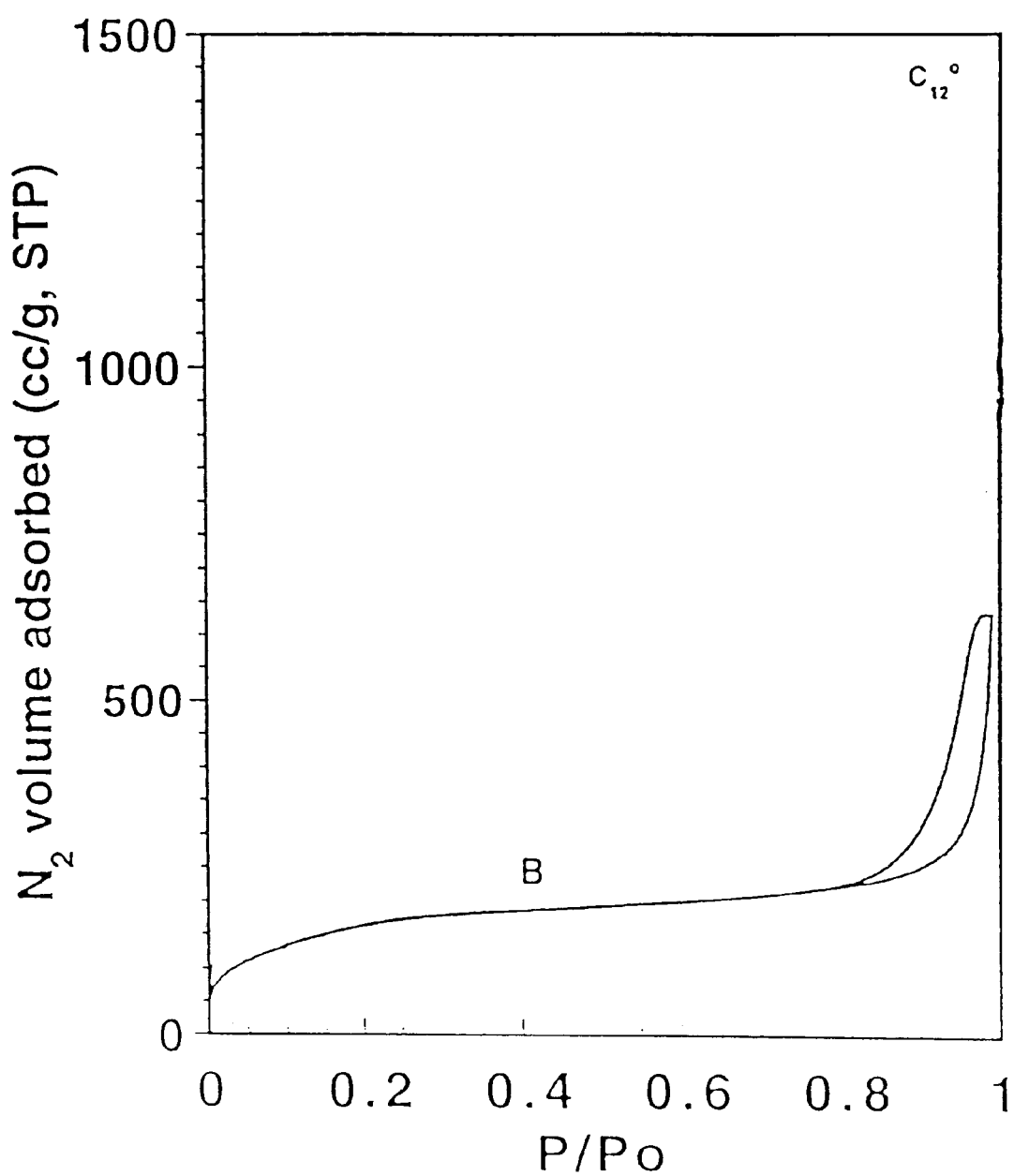
Figure 3C:
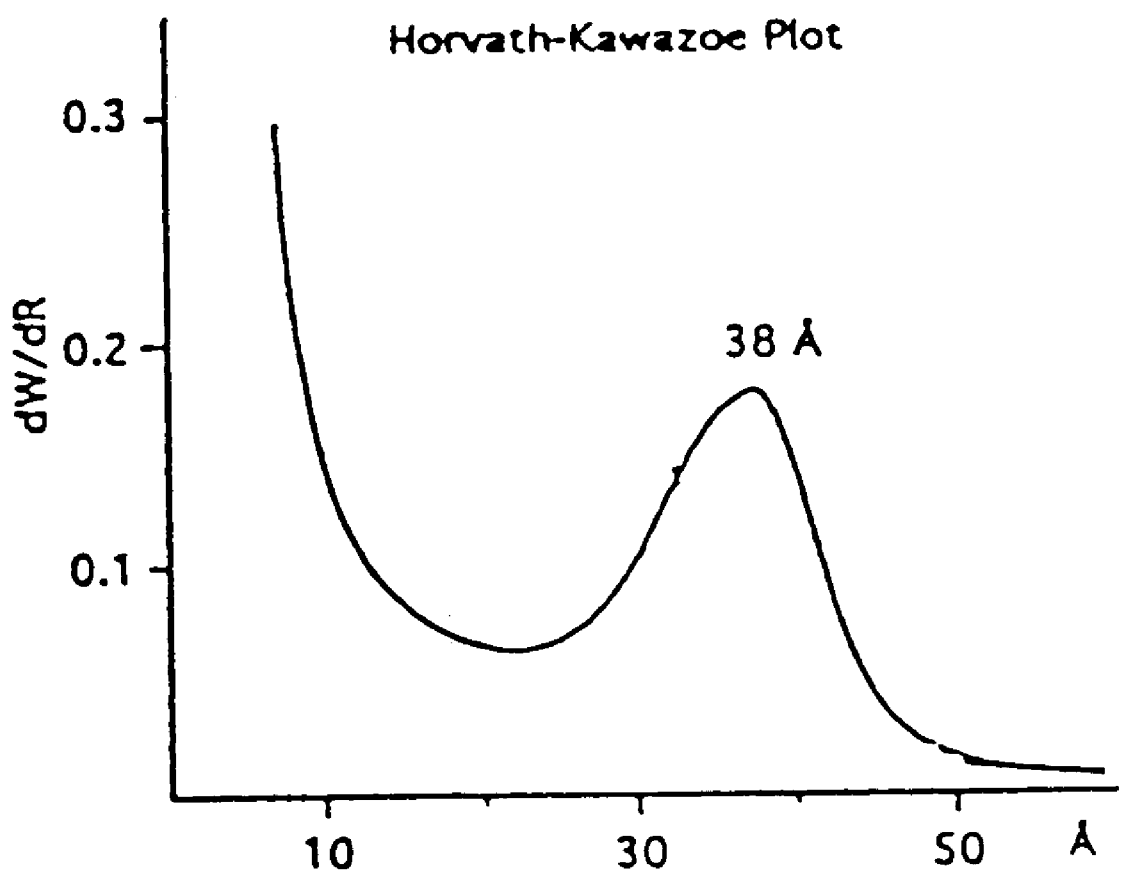
FIG. 3C: Horvath-Kawazoe pore size distribution after calcination at 650° C.

To further probe the influence of mesitylene on the framework pores assembled from a water-rich environment, we repeated the assembly process in 90:10 (v/v) water:ethanol at a much higher Mes/S° ratio of 4.5. As shown by the $N_2$ isotherms in FIG. 3, the adsorption step due to framework pore filling is further shifted to higher relative pressure as a consequence of a HK pore size (38 Å) that is 9 Å larger than the value obtained in the absence of mesitylene. The insert to FIG. 3 shows the half width of the HK pore distribution to be ~10 Å, a value typical of mesoporous molecular sieve materials. On the basis of the hysteresis loop at higher relative pressure, it appears that the textural pore volume is substantially increased by ~50% from ~550 ml STP/g in the absence of mesitylene to ~850 ml STP/g by the presence of mesitylene.

EXAMPLE 6

In order to verify that the textural pores do indeed arise from interparticle voids and not from a large pore component of the framework, the silica molecular sieve assembled from S°=$C_{12}H_{25}NH_2$ at 90:10 (v/v) $H_2O$:ethanol and Mes/S°=4.5 was calcined at 1000° C. to collapse the framework pores. The $N_2$ adsorption/desorption isotherms are given by curve B of FIG. 3. Note that the framework pores indeed have collapsed, as signified by the loss of the pore filling step, but a substantial fraction (>50%) of the textural porosity is retained. Thus, the textural porosity cannot be a consequence of framework structure.

EXAMPLES 7 and 8

Figure 4A:
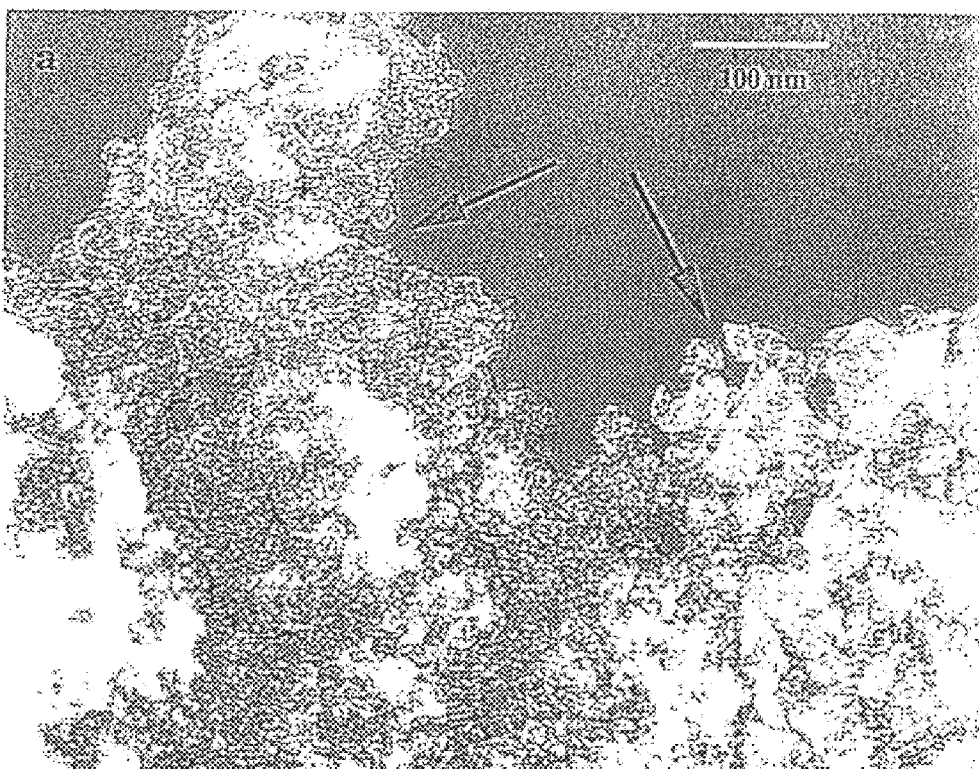
FIGS. 4A to 4D are photographs of TEM images of calcined (650° C.) molecular sieve silicas assembled from dodecylamine and TEOS.
Figure 4B:

The TEM images shown in FIGS. 4A and 4B provide insights into the framework structure and textural mesoporosity associated with silica molecular sieves assembled from water- and ethanol-rich media. Regular framework pores are readily observed, regardless of solvent system used to prepare the products. It is quite clear that the pores originate from the space initially occupied by uniform supramolecular assemblies of surfactant, but there is no apparent long range order to the pore arrangement. Instead the pore packing motif is more wormhole-like, perhaps, even sponge-like, in character.

Figure 4C:
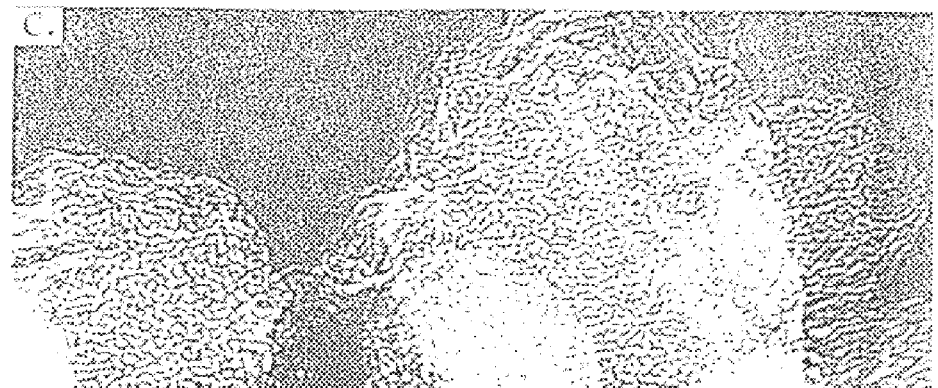
Figure 4D:
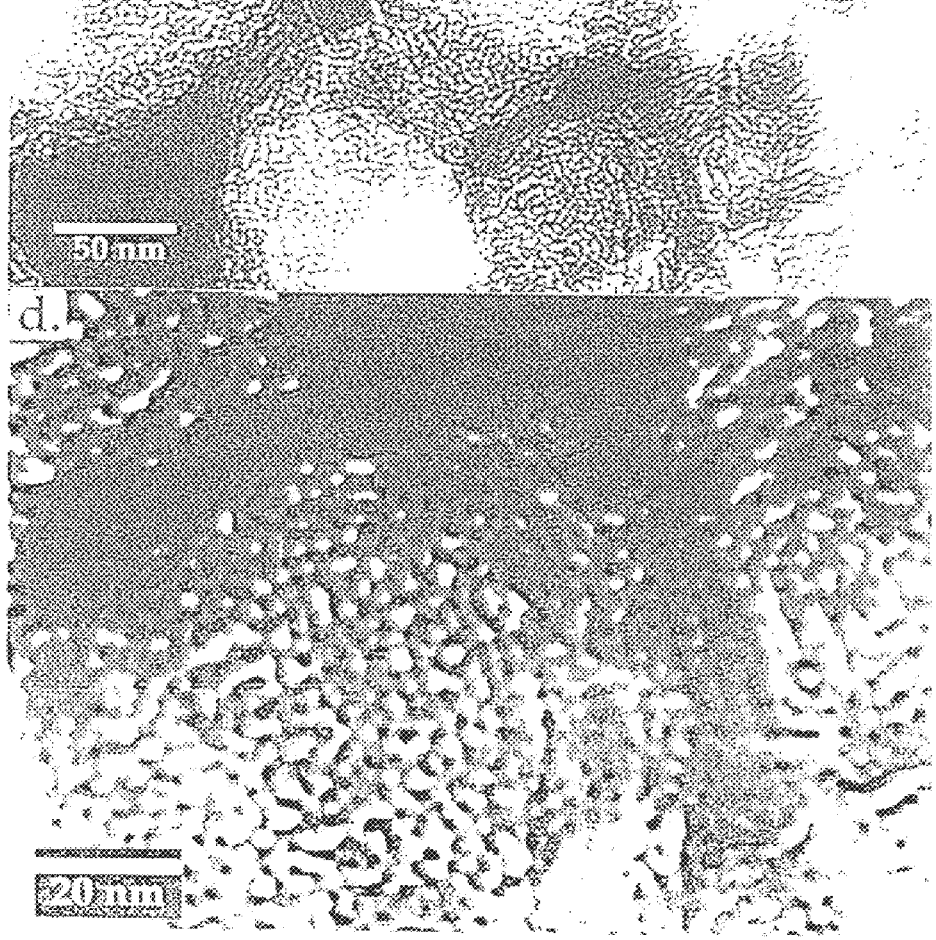

The most important distinguishing feature between the water- and ethanol-rich reaction products is the particle texture. As shown in FIG. 4A, the water-rich reaction mixture yields mesoscale fundamental particles. These fundamental particles aggregate into larger particles with interparticle voids on a mesoscale. These textural mesopores are comparable in size to the mesoscale fundamental particles. In contrast, the ethanol-rich medium forms spheroid to disk-like fundamental particles that are typically 100 nm or larger in size (see FIG. 4B). These macroscale fundamental particles are linked into larger aggregates with a beads-on-a string texture. The interparticle voids are much larger, typically in the macropore range (>50 nm). FIGS. 4C and 4D provide higher resolution images of the wormhole to sponge-like framework structure obtained from water-rich solution.

EXAMPLE 9

Figure 5A:
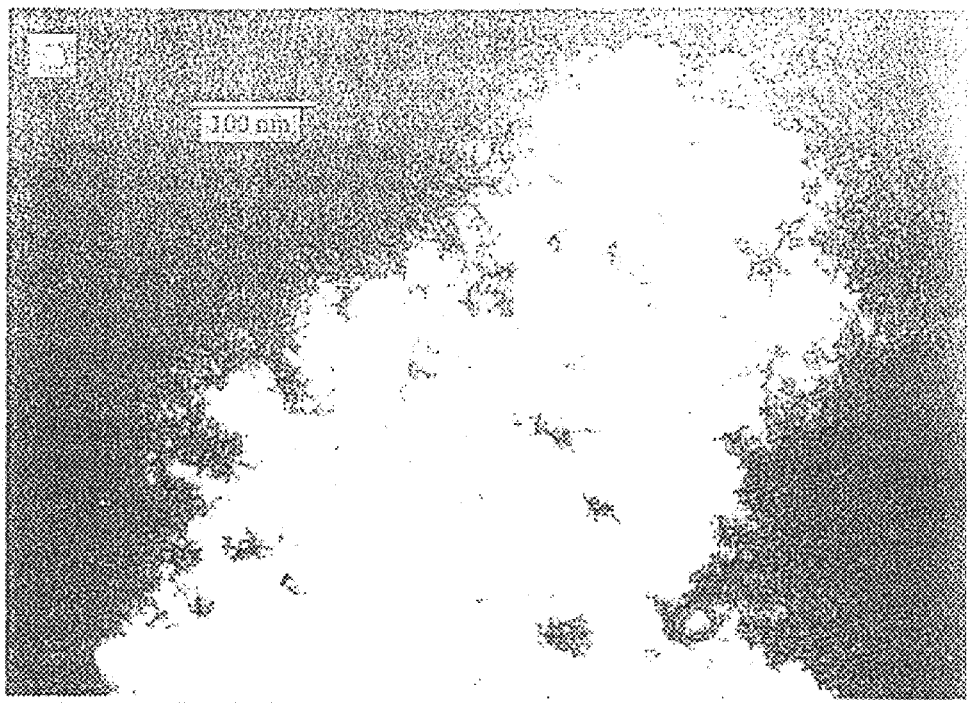
FIGS. 5A and 5B are photographs showing TEM images of the silica molecular sieves prepared from dodecylamine and TEOS in water-rich solution in the presence of mesitylene (Mes/S=4.5) and calcined at 1000° C. to collapse the framework pore structure.
Figure 5B:
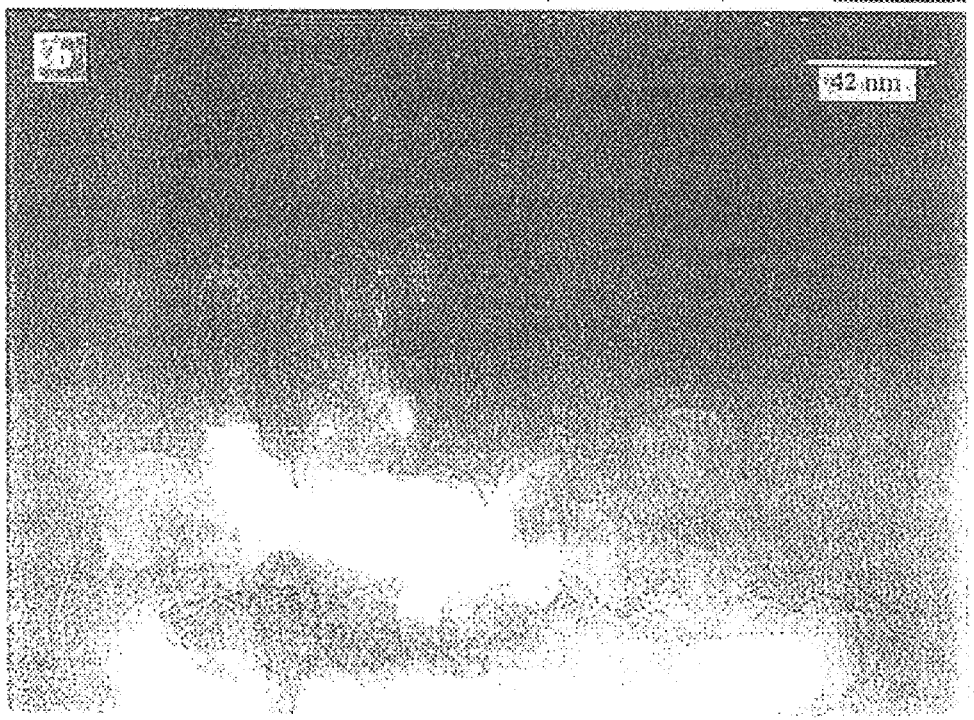

FIGS. 5A and 5B provide TEM images for a silica molecular sieve assembled from water-rich solution in the presence of a relatively high concentration of mesitylene (Mes/S°=4.5) but calcined at 1000° C. to collapse the framework mesopore structure. FIG. 5A, obtained at low magnification, shows the retention of the textural pores. FIG. 5B, obtained at higher magnification, shows that the framework mesopores indeed have been destroyed by thermal treatment. This result, which is consistent with the $N_2$ adsorption results described earlier (cf., FIG. 3), further identifies the interparticle voids as being the origin of the textural mesopores.

EXAMPLES 10, 11, 12, 13 and 14

Figure 6:
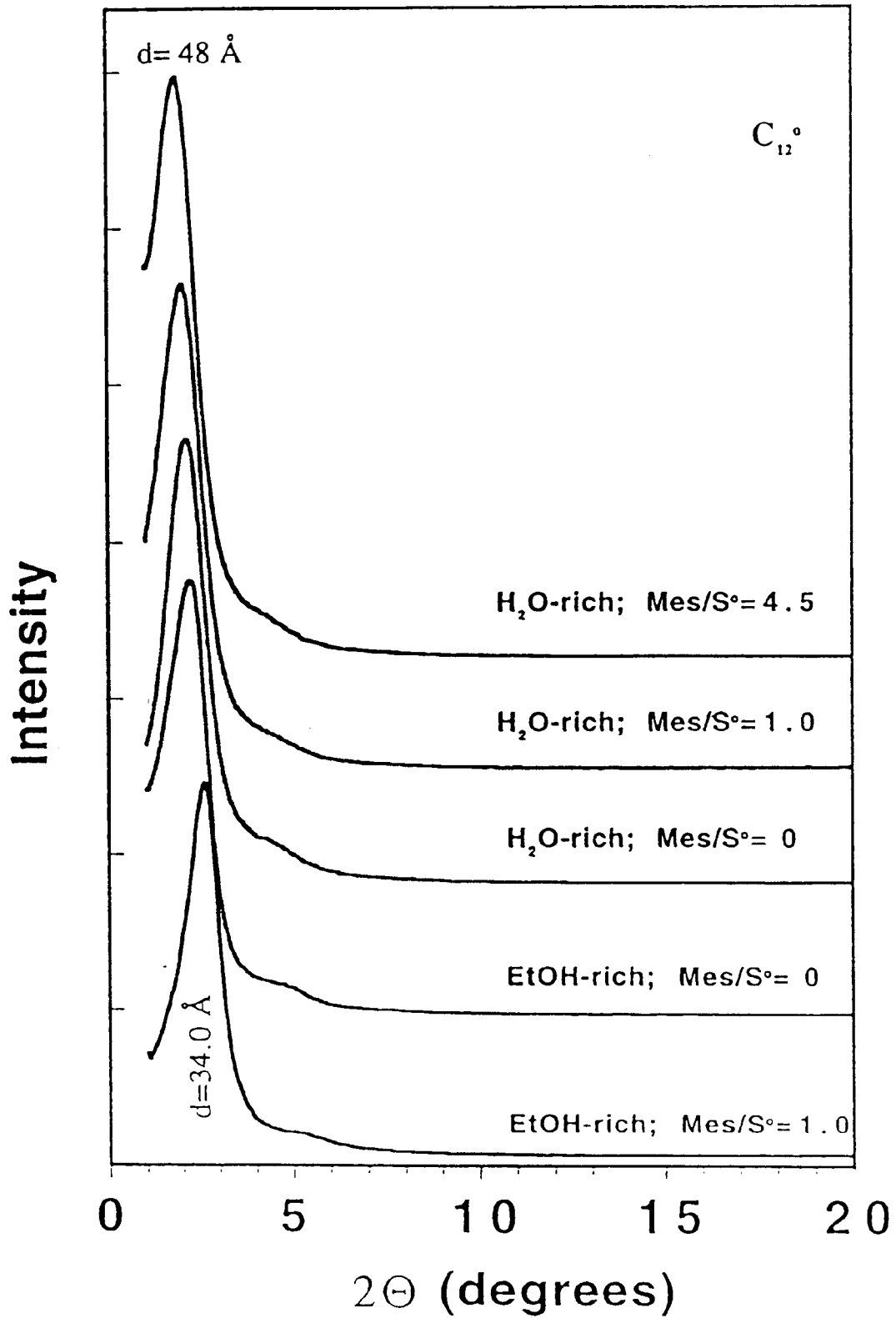
FIG. 6 is a photograph of an x-ray powder diffraction pattern of calcined (650° C.) silica molecular sieves assembled from dodecylamine amine and TEOS in water-rich and ethanol-rich solution with or without mesitylene as an auxiliary structure director.

FIG. 6 provides the X-ray powder diffraction patterns for silica molecular sieves assembled from $C_{12}H_{25}NH_2$ as the structure director. Structures formed from $C_{14}H_{29}NH_2$ showed qualitatively equivalent diffraction features. The patterns all contain a strong, relatively broad reflection at 2.0–3.0°2θ and a very weak broad shoulder in the region near 5.0°2θ. The qualitative form of the patterns is not affected by the water- or ethanol-rich polarity of the assembly medium or by the presence of mesitylene. However, the positions of the intense reflection and the weak broad shoulder are dependent by the polarity of the reaction medium and by the presence of mesitylene.

Table 1 summarizes the basal spacings, HK pore sizes, $N_2$ BET surface areas (SBET), total liquid pore volumes ($V_t$), liquid framework pore volumes ($V_{fr}$), the ratio of textural to framework pore volumes ($V_{tx}/V_{fr}$), and the bulk densities for the silica molecular sieves.

TABLE 1

Physical parameters for calcined (650° C.) molecular sieve silicas prepared by S°I° assembly in $H_2O$-rich and EtOH-rich medium

| S° | Reaction Medium[a] | d (Å) | H-K pore (Å) | $S_{BET}$ m²/g | $V_t$ cc/g | $V_{fr}$ cc/g | $V_{tx}/V_{fr}$ | $d_{bulk}$ g/cc |
|---|---|---|---|---|---|---|---|---|
| $C_{12}H_{25}NH_2$ | $H_2O$-rich; MES/S° = 0 | 41.7 | 29 | 1035 | 1.30 | 0.62 | 1.10 | 0.33 |
| | $H_2O$-rich; MES/S° = 1.0 | 43.3 | 32 | 993 | 1.37 | 0.65 | 1.11 | 0.21 |
| | $H_2O$-rich; MES/S° = 4.5 | 48.0 | 38 | 957 | 1.63 | 0.63 | 1.59 | 0.16 |
| | EtOH-rich; MES/S° = 0 | 39.4 | 28 | 1070 | 0.66 | 0.56 | 0.18 | 0.53 |
| | EtOH-rich; MES/S° = 1.0 | 34.0 | 21 | 1464 | 0.51 | 0.48 | 0.06 | 0.67 |
| $C_{14}H_{29}NH_2$ | $H_2O$-rich; MES/S° = 0 | 44.2 | 34 | 1035 | 1.28 | 0.65 | 0.97 | 0.35 |
| | $H_2O$-rich; MES/S° = 1.0 | 50.2 | 40 | 927 | 1.30 | 0.67 | 0.94 | 0.20 |
| | $H_2O$-rich; MES/S° = 4.5 | 55.2 | 45 | 900 | 1.67 | 0.67 | 1.49 | 0.16 |
| | EtOH-rich; MES/S° = 0 | 49.1 | 33 | 936 | 0.69 | 0.61 | 0.13 | 0.57 |
| | EtOH-rich, MES/S° = 1.0 | 38.7 | 28 | 1117 | 0.62 | 0.57 | 0.09 | 0.65 |

[a]The compositions of $H_2O$-rich and EtOH-rich solutions were 90:10 and 35:65 (v/v) for $H_2O$:EtOH, respectively The basal spacings represented by the strong diffraction line are correlated with the HK pore sizes, even though the framework lacks regular long-range order. The BET surface areas are in the range 700–1500 m²/g. The incorporation of mesitylene into the synthesis of silica molecular sieves from a water-rich medium increases the HK pore size and decreases the surface area of the mesostructure. Conversely, mesitylene decreases the pore sizes and increases the surface areas of silica molecular sieves assembled from ethanol-rich solution.

It is especially noteworthy from the results in Table 1 that the total pore volumes are much larger for the products derived from a water-rich medium (~1.3–1.7 cc/g) than an ethanol-rich medium (~0.5–0.7 cc/g). Yet, the framework pore volumes are confined to the approximate range 0.5–0.7 cc/g. The difference between the total and framework pore volumes is expressed as the textural pore volume, $V_{tx}$. For products assembled from a water-rich medium, the textural pore volume can be up to 1.6 times as large as the framework volume depending on the amount of mesitylene used as a structure modifier. In contrast, the textural pore volume for products obtained from an ethanol-rich medium is equivalent to only a small fraction (6–18%) of the framework volume. Finally, the differences in total pore volumes is manifested in the bulk densities, which are substantially lower for products derived from a water-rich medium (0.16–0.35 g/cc) than an ethanol-rich medium (0.53–0.67 g/cc).

The results of the present invention demonstrate several important advantages of S°I° assembly for the preparation of mesoporous metal oxide molecular sieves. In the case of silica molecular sieves, we have shown through $N_2$ adsorption studies that the textural mesoporosity, which greatly facilitates access to the framework mesopores, can be controlled by a judicious choice of solvent (cf., FIGS. 1 and 2). A water-rich solvent, such as 90:10 (v/v) water:ethanol, promotes the formation of mesopore fundamental particle sizes. TEM images show that the interparticle voids responsible from the textural mesoporosity are on length scale comparable to the fundamental particles (cf., FIG. 4A). Conversely, a solvent of lower polarity, namely, 35:65(v/v) water:ethanol, minimizes the textural porosity by forming much larger fundamental particles (cf., FIG. 4B). There is no doubt that the textural mesoporosity for the product assembled from 90:10 (v/v) water:ethanol arises from interparticle pores. Hysteresis in the $N_2$ adsorption/desorption isotherm show that the textural pores are retained even after the framework pores are thermally collapsed by calcination at 1000° C. (cf., FIG. 3). Thus, the textural porosity can be tailored to a particular materials application by simply controlling the polarity of the solvent for supramolecular assembly.

The relationship between fundamental particle size and solvent polarity most likely is determined by the relative rates of I° hydrolysis and supramolecular assembly in the reaction medium. A water-rich medium leads to rapid nucleation of the mesostructure. For assembly in 90:10 (v/v) water:ethanol, a solid product is formed virtually within minutes of mixing the reagents at ambient temperature. This leads to rapid nucleation and the formation of irregularly shaped fundamental particles. The fundamental particles further aggregate into a self-similar, fractal-like agglomerates (cf., FIG. 4A). However, in the lower polarity 35:65 (v/v) water:ethanol solvent, I° hydrolysis and mesostructure assembly is relatively slow, requiring several hours at ambient temperature for the onset of product formation. The slower nucleation and growth of the mesostructure results in spheroid to disk shaped fundamental particles 100 nm or larger in size. These fundamental particles interpenetrate to form even larger aggregates with interparticle voids beyond the mesopore range (cf., FIG. 4B).

The role of mesitylene as an auxiliary structure director is highly dependent on the polarity of the medium in which mesostructure assembly is carried out. As shown by the results in Table 1 for silicas assembled in the water-rich medium, mesitylene enlarges the framework pores and increases the textural mesoporosity. On the other hand, for assembly in the ethanol-rich medium, mesitylene reduces the framework pore size and decreases still further the already low textural pore volume.

Figure 7:
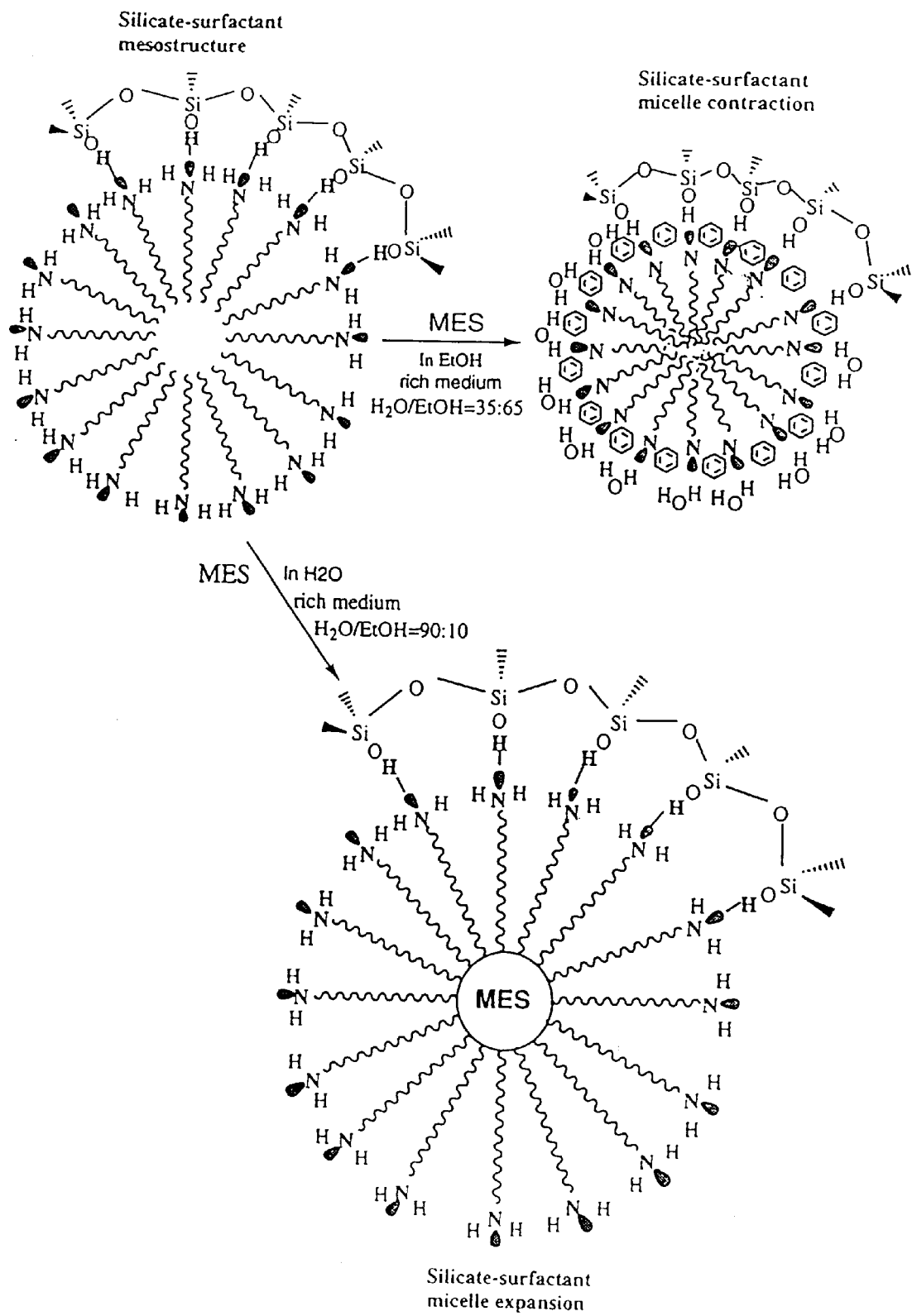
FIG. 7 is a schematic representation of the structure-directing effects of mesitylene on silica molecular sieve assembly. In the water-rich media, the mesitylene "dissolves" in the hydrophobic central core of the micelle leading to pore expansion. In the ethanol-rich environment, mesitylene preferentially "adsorbs" to interfacial head groups, thus increasing effective head group size and subsequently decreasing the pore size.

The role of mesitylene on the framework pore structure is intriguing. Mesitylene is known to bind to surfactant micelles in at least two binding states, namely, in a "dissolved" state at the hydrophobic center of the molecule, and in an "adsorbed" state at the hydrophilic micelle/solvent interface (Mukerjee, P., et al., J. Phys. Chem. 82:1620 (1978); Eriksson, J. E., et al., Acta Chem. Scand., 20:2019 (1966); and Gordon, J. E., et al., J. Phys. Chem. 74:957 (1970)). It is reasonable to expect the equilibrium between these structurally distinct states to depend on the polarity of the solvent in which the surfactant micelles are formed. In accordance with the structurally distinct binding states of mesitylene in surfactant micelles, the mechanism illustrated in FIG. 7 is proposed for the expansion or contraction of the framework pores by mesitylene during the assembly process. In water-rich solvent, in which the solubility of mesitylene is low, the "dissolved" binding state should be favored over the adsorbed state. In this case the size of the micelle will be increased and this will be manifested as an enlarged pore in the mesostructure. But in the lower polarity ethanol-rich solvent, the solubility of mesitylene in the medium will be increased and this will favor binding at the "adsorption" site. Hydrogen bonding between the π-electrons of the aromatic and water dipoles associated with the polar head groups at the micelle-solvent interface is believed to stabilize the adsorbed state of mesitylene (Mukerjee, P., et al., J. Phys. Chem. 82:1620 (1978)). Binding of mesitylene at the micelle surface increases the size of the effective polar head group, leading to a decrease in the radius of curvature, a reduction of micelle size, and a corresponding smaller framework pore size in the mesostructure.

In application Ser. No. 355,979, filed Dec. 14, 1994, describing the assembly of silica molecular sieves in 50:50 (v/v) water:ethanol, it was shown that certain alkylamine surfactants (e.g., dodecylamine) gave derivatives with high textural mesoporosity whereas others afforded relatively low textural pore volumes (e.g., tetradecylamine) (Tanev, P. T., et al., Chem. Mater 8:2068 (1996)). It is now apparent that the degree of textural mesoporosity is quite sensitive to both the solvent polarity and the nature of the S° surfactant. The results of the present work show that dodecylamine and tetradecylamine afford high textural mesoporosity when the solvent is highly polar, as in 90:10 (v/v) water:ethanol (cf., FIGS. 1 and 2).

The preferred materials in Ser. No. 355,979 were described as neutral framework analogs of hexagonal MCM-41 (Tanev, P. T., et al., Science 267:865 (1995)). Evidence for the hexagonal ordering of channels was obtained from selected area electron diffraction (Tanev, P. T., et al., Nature 368:321 (1994)). The X-ray powder diffraction patterns were, attributed to a very small scattering domain size. It is clear from the results of the present invention, however, that the broad diffraction lines characteristic of materials are not due exclusively to a small scattering domain size. The patterns obtained for the fractal-like, fine grained particles are indistinguishable from those obtained for the much larger spheroid to disk-like fundamental particles (cf., FIG. 6). Consequently, framework disorder, in addition to small scattering domain sizes, plays an important role in broadening the diffraction lines. On the basis of the TEM images obtained in the present work (cf., FIGS. 4 and 5), there is no evidence for hexagonal long range channel packing order. Even "disordered" hexagonal channel packing, which has been previously documented for MCM-41 prepared by $S^+I^-$ assembly (Chen, C. Y., et al., Microporus Mater 4:1 (1995)), appears to be difficult to achieve by S°I° assembly.

Wormhole motifs have been observed for silica and alumina mesostructures obtained by N°I° assembly, where N° is a polyoxyethylene surfactant (Bagshaw, S. A., et al., Science 269:1242 (1995); Bagshaw, S. A. et al., Angwen. Chem. Int. Ed. Engl. 35:1102 (1996); and Prouzet, E., et al., Angwen. Chem. Int. Ed. Engl. 36:516 (1997)). Also, sponge-like framework structures have been described for mesoporous silicas obtained by electrostatic $S+I^-$ assembly in the presence of a structure disrupter (e.g., ethylenediaminetetraacetate) (Ryoo, R., et al., J. phy. Chem.

100:17718 (1996)). Distinguishing between wormhole and sponge-like pore structures is not a straight forward matter. "Wormholes" imply channel structures, whereas "sponges" imply reticulated structures. On the basis of the relatively narrow HK pore size distributions observed in the present work and the presence of channel-like voids in the TEM images, the preferred materials of this invention are described as wormhole shaped channels.

The solvents used in the preparation of the compositions of this invention are mixtures of watr and a miscible organic solvent. The water is needed in part to cause hydrolysis of the inorganic precursor and the miscible organic solvent helps to solubilize the structure directing surfactant. The preferred miscible organic solvents are an alkanol containing 1 to 10 carbon atoms. However, other polar organic molecules such as aldehydes hetones, esters and nitrites can be used. In particular, acetone, acetylacetate are suitable substitutes.

The foregoing description is only illustrative of the present invention and the present invention is limited only by the hereinafter appended claims.

We claim:

1. A quasi crystalline inorganic oxide composition having framework-confined mesopores prepared by a method which comprises reacting a neutral amine template and a neutral inorganic oxide precursor wherein the template is dissolved in a solution of water and a miscible organic solvent, containing a larger volume of either the miscible organic solvent or the water, aging of the precipitate and removal of at least some of the template and the aqueous solution to form the quasi crystalline composition which has regular wormhole shaped channels.

2. The composition of claim 1 wherein there is a larger volume of water than the miscible organic solvent, and wherein the composition has, after calcination, a $N_2$ adsorption-desorption isotherm with a hysteresis loop at a partial pressure above about 0.4.

3. The composition of claim 1 wherein the composition has a specific surface area from about 300 to 1500 $m^2/g$.

4. The composition of claim 1 which has an X-ray diffraction pattern with at least one peak corresponding to d-spacing of at least 30 Å.

5. The composition of claim 1 wherein the molar ratio of amine template to inorganic oxide ($IO_m$) before the template has been removed, is between about 0.05 and 3 to 1.

6. The composition of claim 1 wherein the quasi crystalline inorganic oxide composition has the formula:

$$A_xSi_yO_z$$

wherein A is selected from the group consisting of Ca, Mg, Zn, Cu, B, Al, Ga, Cr, Fe, Ge, Ti, V, Zr, V, Sn, W and Mo, x is between 0 and 1.0, y is between about 0 and 1.0 and z is between about 1.0 and 3.0 and the sum of x +y is equal to 1.0.

7. The composition of claim 6 wherein A is Al, x is between 0 and 0.33 and y is between 0.67 and 1.00, and z is between 1.8 and 2.0 when sum of x+y is equal to 1.0.

8. The composition of claim 1 containing the template.

9. The composition of claim 1 with out the template which has been removed by extraction with a solvent for the template.

10. The composition of claim 1 which is calcined.

11. A composite material prepared from the composition of claim 1 admixed with a material selected from the group consisting of amorphous, quasi crystalline and crystalline materials.

12. The composition of claim 1 which is calcined and then in addition impregnated with at least one metal compound or element in the mesopores.

13. The composition of claim 1 which has been calcined and contains an organometallic compound in the mesopores.

14. The composition of claims 12 and 13 in which the metal compound, metallic element or organometallic compound is selected from the group consisting of Cu, Co, Cr, Ni, Fe, Ti, V, W, Mo, Pt, Pd, Ir and Sn.

15. The composition of claim 1 wherein the solution of the template contains an organic compound which is essentially insoluble in water and soluble in the watr miscible organic solvent.

16. The composition of claim 15 wherein the organic compound is mesitylene.

* * * * *

UNITED STATES PATENT AND TRADEMARK OFFICE
CERTIFICATE OF CORRECTION

PATENT NO. : 6,410,473 B1  Page 1 of 2
DATED : June 25, 2002
INVENTOR(S) : Thomas J. Pinnavaia et al.

It is certified that error appears in the above-identified patent and that said Letters Patent is hereby corrected as shown below:

Title page,
Item [56], OTHER PUBLICATIONS, "Barrer, et al., Zeolites, vol. 1, 30-140 (1981)" should be -- Barrer, et al., Zeolites, vol. 1, 130-140 (1981) --.

Column 3,
Line 66, "species (I)" should be -- species ($I^-$) --.

Column 4,
Line 3, "($S^=$) was used" should be -- ($S^-$) was used --.
Line 4, "species (I+) via $S^=I^+$ ion" should be -- species ($I^+$) via $S^-I^+$ ion --.
Line 9, "type $S^+X^{-1+}$" should be -- type $S^+X^-I^+$ --.
Line 11, "X=Cl, Br)" should be -- $X^-$=$Cl^-$ $Br^-$ --.

Column 5,
Line 32, "volume ≲ 0.6 cm" should be -- volume ≤ 0.6 cm --.

Column 7,
Line 14, "minus 200° and plus 1000°C" should be -- minus 20° and plus 100°C --.

Column 8,
Line 58, "atoms (2<m<8)" should be -- atoms (2≤m≤8) --.

Column 10,
Line 62, "$(OC_2H_5)_2$]OH" should be -- $(OC_2H_5)_2]_nOH$ --.

Column 13,
Line 27, "(λX=1.542" should be -- (λ=1.542 --.

Column 16,
Line 20, "(SBET)" should be -- ($S_{BET}$) --.

UNITED STATES PATENT AND TRADEMARK OFFICE
CERTIFICATE OF CORRECTION

PATENT NO.   : 6,410,473 B1
DATED        : June 25, 2002
INVENTOR(S)  : Thomas J. Pinnavaia et al.

It is certified that error appears in the above-identified patent and that said Letters Patent is hereby corrected as shown below:

<u>Column 18,</u>
Line 65, "$S+\bar{I}$ assembly" should be -- $S^+\bar{I}$ assembly --.

<u>Column 19,</u>
Line 10, "mixtures of watr and" should be -- mixtures of water and --.
Line 16, "hetones" should be -- ketones --.
Line 16, "nitrites" should be -- nitriles --.

<u>Column 20,</u>
Line 37, "watr miscible" should be -- water miscible --.

Signed and Sealed this

Twenty-fifth Day of March, 2003

JAMES E. ROGAN
*Director of the United States Patent and Trademark Office*